United States Patent
Madenjian et al.

(10) Patent No.: US 10,766,871 B2
(45) Date of Patent: Sep. 8, 2020

(54) PROCESS FOR THE EPOXIDATION OF PROPENE TO PROPYLENE OXIDE

(71) Applicants: BASF SE, Ludwigshafen am Rhein (DE); Dow Global Technologies LLC, Midland, MI (US)

(72) Inventors: Edward O. Madenjian, Lake Jackson, TX (US); Kenric A. Marshall, Lake Jackson, TX (US)

(73) Assignees: BASF SE, Ludwigshafen am Rhein (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/061,725

(22) PCT Filed: Dec. 16, 2016

(86) PCT No.: PCT/EP2016/081498
§ 371 (c)(1),
(2) Date: Jun. 13, 2018

(87) PCT Pub. No.: WO2017/103151
PCT Pub. Date: Jun. 22, 2017

(65) Prior Publication Data
US 2019/0002422 A1    Jan. 3, 2019

Related U.S. Application Data

(60) Provisional application No. 62/267,926, filed on Dec. 16, 2015.

(51) Int. Cl.
*C07D 301/12*    (2006.01)
*B01J 29/89*    (2006.01)
(Continued)

(52) U.S. Cl.
CPC ............ *C07D 301/12* (2013.01); *B01J 29/89* (2013.01); *B01J 31/0259* (2013.01); *B01J 31/38* (2013.01);
(Continued)

(58) Field of Classification Search
CPC ..... C07D 301/12; B01J 31/0259; B01J 31/38; B01J 29/89; B01J 2531/002; B01J 2231/72
(Continued)

(56) References Cited

U.S. PATENT DOCUMENTS

| 4,824,976 A | 4/1989 | Clerici et al. |
| 4,833,260 A | 5/1989 | Neri et al. |
| 5,591,875 A | 1/1997 | Chang et al. |

FOREIGN PATENT DOCUMENTS

| EP | 0 757 045 A1 | 2/1997 |
| WO | WO 2015/010994 A1 | 1/2015 |

OTHER PUBLICATIONS

U.S. Pat. No. 9,725,428, Aug. 8, 2017, 2016/0176834, Teles et al.
(Continued)

*Primary Examiner* — Taylor V Oh
(74) *Attorney, Agent, or Firm* — Oblon, McClelland, Maier & Neustadt, L.L.P.

(57) ABSTRACT

A continuous process for the preparation of propylene oxide, comprising providing a liquid feed stream comprising propene, hydrogen peroxide, methanol, water, at least one dissolved potassium salt of hydroxyethylidenediphosphonic acid, and optionally propane; passing the liquid feed stream provided in (i) into an epoxidation reactor comprising a catalyst comprising a titanium zeolite of structure type MFI, and subjecting the liquid feed stream to epoxidation reaction conditions in the epoxidation reactor, obtaining a reaction mixture comprising propylene oxide, methanol, water, and
(Continued)

the at least one dissolved potassium salt of hydroxyethylidenediphosphonic acid, and optionally propane; removing an effluent stream from the epoxidation reactor, the effluent stream comprising propylene oxide, methanol, water, at least a portion of the at least one potassium salt of hydroxyethylidenediphosphonic acid, and optionally propane.

20 Claims, 20 Drawing Sheets

(51) Int. Cl.
  *B01J 31/02* (2006.01)
  *B01J 31/38* (2006.01)
(52) U.S. Cl.
  CPC ...... *B01J 2231/72* (2013.01); *B01J 2531/002* (2013.01)
(58) Field of Classification Search
  USPC .......................................................... 549/531
  See application file for complete search history.

(56) References Cited

OTHER PUBLICATIONS

U.S. Pat. No. 9,688,648, Jun. 27, 2017, 2016/0185741, Teles et al.
U.S. Pat. No. 9,738,616, Aug. 22, 2017, 2016/0176835, Riedel et al.
U.S. Pat. No. 10,053,439, Aug. 21, 2018, 2017/0298034, Riedel et al.
International Search Report and Written Opinion dated Feb. 13, 2017, in PCT/EP2016/081498, filed Dec. 16, 2016.

□ K-ATMP as buffer    ▽ K₂-ATMP as buffer

PROCESS FOR THE EPOXIDATION OF PROPENE TO PROPYLENE OXIDE

The present invention relates to a novel process for the production of propylene oxide using at least one potassium salt of hydroxyethylidenediphosphonic acid as an additive as well as to the use of at least one potassium salt of hydroxyethylidenediphosphonic acid as an additive in a process for the preparation of propylene oxide. Further, this invention relates to a novel a catalytic system to be employed in such a process and to the use of such a catalytic system in a process for the epoxidation of propene.

It is well-known that the epoxidation of olefinic compounds such as propene with hydrogen peroxide may be effectively catalyzed employing synthetic zeolites containing titanium atoms as described in, for example, U.S. Pat. No. 4,833,260. However, a well-known problem is the formation of organic by-products resulting from the non-selective ring-opening reactions that take place when the epoxidation is carried out in a protic medium such as water or an alcohol, which results in lower selectivities for the process. This is described in, for example, U.S. Pat. No. 4,824,976. It is also well-known that non-selective hydrogen peroxide decomposition to oxygen and water tends to gradually increase as the catalyst ages, which can result in catalyst fouling and reagent loss issues due to the high loadings of oxygen derived from the decomposition of hydrogen peroxide.

Regarding the first issue, it has been found that the use of certain additives that can act as acid neutralizing agents leads to improved processes by reducing the quantity of ring-opened by-products formed (see U.S. Pat. No. 4,824,976). Potassium hydrogen phosphate, $K_2HPO_4$ is such an additive. However, while the use of this additive results in the catalyst lasting longer and in higher selectivities, increasing the concentration of $K_2HPO_4$ reduces the formation of organic-based byproducts but concurrently increases the formation of oxygen from the decomposition of hydrogen peroxide. European application EP 0 757 045 A relates to the addition of a salt as well as a chelating agent either separately or as part of the same compound in olefin epoxidation processes in order to overcome the above-mentioned issues. Thus, there is a need for the provision of suitable additives that can be employed in industrial olefin epoxidation processes in which the formation of organic by-products and the decomposition of hydrogen peroxide can be addressed simultaneously.

It was surprisingly found that the use of at least one potassium salt of hydroxyethylidenediphosphonic acid to the reactor in a continuous process for the epoxidation of propylene to propylene oxide employing a catalyst comprising a titanium zeolite of structure type MFI results in the formation of reduced quantities of oxygen from the decomposition of hydrogen peroxide while producing an equivalent level of organic by-products to that produced in a system using other additives. Since oxygen is at such a reduced level, the formation of organic by-products can be suppressed further by increasing the concentration of the additive. Thus, as opposed to other processes in which the formation of organic by-products is reduced at the expense of an increased oxygen formation, the use of at least one potassium salt of hydroxyethylidenediphosphonic acid advantageously addresses both issues at the same time.

Therefore, the present invention relates to a continuous process for the preparation of propylene oxide, comprising
(i) providing a liquid feed stream comprising propene, hydrogen peroxide, methanol, water, at least one dissolved potassium salt of hydroxyethylidenediphosphonic acid, and optionally propane;
(ii) passing the liquid feed stream provided in (i) into an epoxidation reactor comprising a catalyst comprising a titanium zeolite of structure type MFI, and subjecting the liquid feed stream to epoxidation reaction conditions in the epoxidation reactor, obtaining a reaction mixture comprising propylene oxide, methanol, water, and the at least one dissolved potassium salt of hydroxyethylidenediphosphonic acid, and optionally propane;
(iii) removing an effluent stream from the epoxidation reactor, the effluent stream comprising propylene oxide, methanol, water, at least a portion of the at least one potassium salt of hydroxyethylidenediphosphonic acid, and optionally propane.

In the context of the present invention, the term "hydroxyethylidenediphosphonic acid" (HEDP) refers to the compound of formula (I)

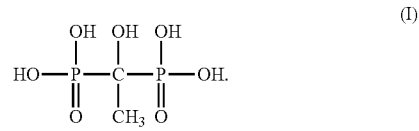

Thus, the term "potassium salt of hydroxyethylidenediphosphonic acid" encompasses all possible potassium salts of hydroxyethylidenediphosphonic acid, i.e. the mono-, di-, tri- and tetrapotassium salts of the mono-, di-, tri- and tetraanionic, deprotonated conjugates of hydroxyethylidenediphosphonic acid.

Step (i)

Regarding the molar ratio of potassium relative to phosphorus in the at least one potassium salt of hydroxyethylidenediphosphonic acid, no specific limitation exists. Preferably, the molar ratio of potassium relative to phosphorus in the at least one potassium salt of hydroxyethylidenediphosphonic acid is in the range of from 1:2 to 2:1, preferably from 1:2 to 1.5:1. More preferably, the molar ratio of potassium relative to phosphorus in the at least one potassium salt of hydroxyethylidenediphosphonic acid is in the range of from 0.75:1 to 1.25:1, more preferably in the range of from 0.9:1 to 1.1:1.

Therefore, it is preferred that the at least one potassium salt of hydroxyethylidene-diphosphonic acid comprises the dipotassium salt of hydroxyethylidenediphosphonic acid.

According to the present invention, it is preferred that the liquid feed stream provided in (i) comprises the dipotassium salt of hydroxyethylidenediphosphonic acid as the at least one dissolved potassium salt of hydroxyethylidenediphosphonic acid.

Regarding the molar ratio of the potassium comprised in the at least one potassium salt of hydroxyethylidenediphosphonic acid relative to the hydrogen peroxide in the liquid feed stream provided in (i), no specific limitation exists. Preferably, the molar ratio of the potassium comprised in the at least one potassium salt of hydroxyethylidenediphosphonic acid relative to the hydrogen peroxide in the liquid feed stream provided in (i) is in the range of from $5 \times 10^{-6}:1$ to $1000 \times 10^{-6}:1$, preferably from $10 \times 10^{-6}:1$ to $700 \times 10^{-6}:1$, more preferably from $10 \times 10^{-6}:1$ to $500 \times 10^{-6}:1$.

Regarding the molar ratio of the potassium in the liquid feed stream provided in (i) relative to the potassium comprised in the at least one potassium salt of hydroxyethylidenediphosphonic acid in the liquid feed stream provided in (i), no specific limitation exists. Preferably, the molar ratio of the potassium in the liquid feed stream provided in (i) relative to the the potassium comprised in the at least one potassium salt of hydroxyethylidenediphosphonic acid in the liquid feed stream provided in (i) is in the range of from 1.2:1 to 1:1, preferably from 1.1:1 to 1:1, more preferably from 1.05:1 to 1:1.

It is preferred that, in the liquid feed stream provided in (i), the amount of potassium not derived from the at least one potassium salt of hydroxyethylidenediphosphonic acid is at most 100 weight-ppm, preferably at most than 10 weight-ppm, more preferably at most than 1 weight-ppm, based on the total weight of the liquid feed stream.

Regarding the molar ratio of the phosphorus in the liquid feed stream provided in (i) relative to the phosphorus comprised in the at least one potassium salt of hydroxyethylidene-diphosphonic acid in the liquid feed stream provided in (i), no specific limitation exists. Preferably, the molar ratio of the phosphorus in the liquid feed stream provided in (i) relative to the phosphorus comprised in the at least one potassium salt of hydroxyethylidene-diphosphonic acid in the liquid feed stream provided in (i) is in the range of from 1.2:1 to 1:1, preferably from 1.1:1 to 1:1, more preferably from 1.05:1 to 1:1.

It is preferred that, in the liquid feed stream provided in (i), the amount of phosphorus not derived from the at least one potassium salt of hydroxyethylidenediphosphonic acid at most 100 weight-ppm, preferably at most 10 weight-ppm, more preferably at most 1 weight-ppm, based on the total weight of the liquid feed stream.

Regarding the molar ratio of sodium relative to hydrogen peroxide in the liquid feed stream provided in (i), no specific limitation exists. Preferably, the molar ratio of sodium relative to hydrogen peroxide in the liquid feed stream provided in (i) is in the range of from $1\times10^{-6}$:1 to $250\times10^{-6}$:1, preferably from $5\times10^{-6}$:1 to $50\times10^{-6}$:1.

Regarding the amount of ammonium $NH_4^+$ comprised in the liquid feed stream provided in (i), no specific limitation exists. Preferably, the ammonium $NH_4^+$ in the liquid feed stream provided in (i) is comprised in an amount of at most 2 weight-ppm, preferably at most 1 weight-ppm, based on the total weight of the liquid feed stream.

It is preferred that at least 95 weight-%, preferably from 95 to 100 weight-%, more preferably from 98 to 100 weight-%, more preferably from 99 to 100 weight-% of the liquid feed stream provided in (i) consist of the propene, the hydrogen peroxide, the methanol, the water, the at least one dissolved potassium salt of hydroxyethylidenediphosphonic acid, and optionally propane.

It is preferred that in (i), the liquid feed stream is provided by combining a stream comprising hydrogen peroxide and optionally water, a stream comprising methanol and optionally water, and a stream comprising propene and optionally propane, and wherein prior to combining these streams, an aqueous stream comprising the at least one dissolved potassium salt of hydroxyethylidenediphosphonic acid is admixed either with the stream comprising hydrogen peroxide and optionally water, or with the stream comprising methanol and optionally water, or with the stream comprising propene and optionally propane, or with a mixed stream of two or three of these streams.

It is also preferred that in (i), the liquid feed stream is provided by combining a stream comprising hydrogen peroxide and optionally water, a stream comprising methanol and optionally water, and a stream comprising propene and optionally propane, and wherein prior to combining these streams, an aqueous stream comprising the at least one dissolved potassium salt of hydroxyethylidenediphosphonic acid is admixed with the stream comprising hydrogen peroxide and optionally water, or with the stream comprising methanol and optionally water, or with a mixed stream thereof.

Regarding the concentration of the at least one potassium salt of hydroxyethylidenediphosphonic acid in the aqueous stream comprising the at least one potassium salt of hydroxyethylidenediphosphonic acid, no specific limitation exists. Preferably, the concentration of the at least one potassium salt of hydroxyethylidene-diphosphonic acid in the aqueous stream comprising the at least one potassium salt of hydroxyethylidenediphosphonic acid is in the range of from 0.1 to 50 weight %, preferably from 0.2 to 45 weight %, more preferably from 0.5 to 40 weight % based on the total weight of the aqueous stream comprising the at least one potassium salt of hydroxyethylidene-diphosphonic acid.

Regarding the stream comprising hydrogen peroxide and optionally water, no specific limitation exists. Preferably, the stream comprising hydrogen peroxide and optionally water is an aqueous hydrogen peroxide stream having a hydrogen peroxide concentration in the range of from 25 to 75 weight-%, preferably from 30 to 50 weight-%, based on the total weight of the aqueous hydrogen peroxide stream.

According to the present invention, the aqueous hydrogen peroxide stream may further comprise sodium. Preferably, the aqueous hydrogen peroxide stream further comprises sodium with a molar ratio of sodium relative to hydrogen peroxide in the range of from $1\times10^{-6}$:1 to $250\times10^{-6}$, preferably from $5\times10^{-6}$:1 to $50\times10^{-6}$:1.

Step (ii)

Regarding the temperature of the liquid feed stream passed into the epoxidation reactor, no specific limitation exists. Preferably, the liquid feed stream passed into the epoxidation reactor in (ii) has a temperature in the range of from 0 to 60° C., preferably from 25 to 50° C.

Regarding the pressure of the liquid feed stream passed into the epoxidation reactor, no specific limitation exists. Preferably, the liquid feed stream passed into the epoxidation reactor in (ii) is at a pressure in the range of from 14 to 100 bar, preferably from 15 to 32 bar, more preferably from 15 to 25 bar.

According to the present invention, the temperature of the reaction mixture in (ii) is controlled using a heat transfer medium, preferably by passing the heat transfer medium through a jacket of the epoxidation reactor.

Regarding the temperature of the epoxidation conditions in (ii), no specific limitation exists. Preferably, in (ii), the epoxidation conditions comprise an epoxidation reaction temperature in the range of from 10 to 100° C., preferably from 30 to 80° C., more preferably from 40 to 65° C., wherein the epoxidation reaction temperature is defined as the temperature of the heat transfer medium prior to controlling of the temperature of the reaction mixture, preferably as the temperature of the heat transfer medium at the entrance of the jacket of the epoxidation reactor.

Regarding the pressure of the epoxidation conditions in (ii), no specific limitation exists. Preferably, in (ii), the epoxidation conditions comprise an epoxidation reaction pressure in the range of from 14 to 100 bar, preferably from 15 to 32 bar, more preferably from 15 to 25 bar, wherein the epoxidation reaction pressure is defined as the pressure at the exit of the epoxidation reactor.

Regarding the amount of catalyst in (ii), no specific limitation exists. Preferably, in (ii), the epoxidation conditions comprise a catalyst loading in the range of from 0.05 to 1.25 $h^{-1}$, preferably from 0.1 to 1 $h^{-1}$, more preferably from 0.2 to 0.7 h$^{-1}$, wherein the catalyst loading is defined as the ratio of the mass flow rate in kg/h of hydrogen peroxide contained in liquid feed stream provided in (i) divided by the amount in kg of catalyst comprising a titanium zeolite of structure type MFI comprised in the epoxidation reactor in (ii).

Step (iii)

According to step (iii), an effluent stream is removed from the epoxidation reactor wherein the effluent stream comprises propylene oxide, methanol, water, at least a portion of the at least one potassium salt of hydroxyethylidenediphosphonic acid, and optionally propane. Generally, it is conceivable that in the epoxidation reaction according to (ii), the hydrogen peroxide contained in the stream subjected to (ii) is completely converted. Preferably, the hydrogen peroxide conversion in (ii) is below 100%, such as in the range of from 90 to 99%, preferably of from 90 to 98%. Therefore, it is preferred that the effluent stream removed in (iii) contains hydrogen peroxide. This hydrogen peroxide may be separated from the effluent stream in a suitable manner. It is preferred that the effluent stream containing hydrogen peroxide is subjected to at least one further epoxidation step, more preferably one further epoxidation step. It is further preferred that the effluent stream, prior to being subjected to a further epoxidation step, is subjected to an intermediate separation step wherein propylene oxide contained in the effluent stream is suitably separated from the effluent stream and the remaining stream, depleted of propylene oxide and comprising methanol, water, at least a portion of the at least one potassium salt of hydroxyethylidenediphosphonic acid optionally propene and optionally propane, is subjected to a further epoxidation step. Thus intermediate separation step can be carried out by any suitable separation method or combination of separation methods; preferably, the intermediate separation is carried out by rectification, preferably by distillation, preferably in a distillation tower.

Additional Steps (iv) to (vi)

Therefore, the effluent stream removed in (iii) preferably additionally comprises hydrogen peroxide and optionally propene, and the process further comprises (iv) separating propylene oxide from the effluent stream, obtaining a stream being depleted in propylene oxide and comprising hydrogen peroxide, methanol, water, at least a portion of the at least one potassium salt of hydroxyethylidenediphosphonic acid, optionally propene and optionally propane;

(v) passing the stream being depleted in propylene oxide and comprising hydrogen peroxide, methanol, water, at least a portion of the at least one potassium salt of hydroxyethylidenediphosphonic acid optionally propene and optionally propane obtained in (iv) into an epoxidation reactor comprising a catalyst comprising a titanium zeolite of structure type MFI, and subjecting the stream to epoxidation reaction conditions in the epoxidation reactor, obtaining a reaction mixture comprising propylene oxide, methanol, water, the portion of the at least one dissolved potassium salt of hydroxyethylidenediphosphonic acid, and optionally propane;

(vi) removing an effluent stream from the epoxidation reactor, the effluent stream comprising propylene oxide, methanol, water, at least a portion of the portion of the at least one potassium salt of hydroxyethylidenediphosphonic acid, and optionally propane.

Regarding the temperature in the epoxidation conditions in (v), no specific limitation exists. Preferably, in (v), the epoxidation conditions comprise adiabatic epoxidation reaction conditions.

Regarding the catalyst loading in the epoxidation conditions in (v), no specific limitation exists. Preferably, in (v), the epoxidation conditions comprise a catalyst loading in the range of from 0.01 to 0.2 h$^{-1}$, preferably of from 0.015 to 0.15 h$^{-1}$, more preferably of from 0.03 to 0.1 h$^{-1}$, wherein the catalyst loading is defined as the ratio of the mass flow rate in kg/h of hydrogen peroxide contained in the stream stream being depleted in propylene oxide and comprising hydrogen peroxide, methanol, water, at least a portion of the at least one potassium salt of hydroxyethylidenediphosphonic acid optionally propene and optionally propane obtained in (iv) divided by the amount in kg of catalyst comprising a titanium zeolite of structure type MFI comprised in the epoxidation reactor in (v).

Preferably, according to the present invention, the epoxidation conditions comprise a hydrogen peroxide conversion in the range of from 90 to 100%, preferably from 95 to 100%, more preferably from 99 to 100%, wherein the hydrogen peroxide conversion is calculated based on the amount of hydrogen peroxide comprised in the effluent stream removed in (iii), preferably in (vi), relative to the amount of hydrogen peroxide comprised in the liquid feed stream provided in (i).

Catalyst Employed in (ii) or in (ii) and (v)

Titanium zeolites having MFI-structure can be identified by means of a specific x-ray diffraction pattern as well as by lattice vibration band in the infrared region at about 960 cm$^{-1}$. The titanium zeolites thus differ from alkali metal titanates as well as from crystalline and amorphous TiO$_2$-phases.

The at least one titanium zeolite can additionally contain elements selected from the group consisting of the groups IIA, IVA, VA, VIA, VIIA, VIIIB, IB, IIB, IIIB, IVB, and VB of the periodic table, such as, for example, aluminum, boron, zirconium, chromium, tin, zinc, gallium, germanium, vanadium, iron, niobium, cobalt, nickel, or mixtures of two or more of these elements. If the catalyst contains two or more titanium zeolites, for example five, four, three or two titanium zeolites, these titanium zeolites can contain the same or different additional elements or different mixtures of two or more of these elements. Most preferably, the titanium zeolite of the present invention essentially consists of Si, O, and Ti.

The titanium zeolite contained in the catalyst according to (i) can in principle be prepared by any conceivable method. Typically, the synthesis of the at least one titanium zeolite according to the present invention is carried out in hydrothermal systems involving the combination of an active source of silicon oxide and a titanium source, such as titanium oxide, with at least one template compound capable of forming the desired titanium zeolite in an aqueous suspension, for example in a basic suspension. Typically, organic templates are employed. Preferably, the synthesis is carried out at elevated temperatures, for example temperatures in the range of from to 150 to 200° C., preferably from 160 to 180° C.

In principle, any suitable compound can be used as silicon oxide source. Typical sources of silicon oxide (SiO$_2$) include silicates, silica hydrogel, silicic acid, colloidal silica, fumed silica, tetraalkoxysilanes, silicon hydroxides, precipitated silica and clays. Both so-called "wet-process silicon dioxide" and so-called "dry-process" silicon dioxide can be employed. In these cases, the silicon dioxide is particularly preferably amorphous, wherein the size of the silicon dioxide particles is, for example, in the range of from 5 to 100 nm and the surface area of the silicon dioxide particles is, for example, in the range of from 50 to 500 m$^2$/g. Colloidal silicon dioxide is, inter alia, commercially available as Ludox®, Syton®, Nalco®, or Snowtex®. "Wet process" silicon dioxide is, inter alia, commercially available as Hi-Sil®, Ultrasil®, Vulcasil®, Santocel®, Valron-Estersil®, Tokusil® or Nipsil®. "Dry process" silicon dioxide is commercially available, inter alia, as Aerosil®, Reolosil®, Cab-O-Sil®, Fransil® or ArcSilica®. It is as well within the scope of the present invention to use a silicon dioxide precursor compound as silicon oxide source. For example, tetraalkoxysilanes, such as for example, tetraethoxysilane or tetrapropoxysilane, may be mentioned as precursor compound.

As template, any template suitable to provide the desired zeolitic structure can be used. Preferably, tetrapropylammonium hydroxide, more preferably tetra-n-propylammonium hydroxide is employed where a titanium zeolite having MFI structure, also known as titanium silicalite-1 (TS-1) is prepared.

Preferably, the at least one pore forming agent is removed in a later step by calcination, as described below.

Typically, the synthesis of the titanium zeolite is carried out batchwise in an autoclave so that the reaction suspension is subjected at autogenous pressure for a number of hours or a few days until the titanium zeolite is obtained. According to a preferred embodiment of the present invention, the synthesis generally proceeds at elevated temperatures wherein the temperatures during the hydrothermal crystallization step are typically in the range of from 150 to 200° C., preferably in the range of from 160 to 180° C. Usually, the reaction is carried out for a time in the range of a few hours to several days, preferably for a time in the range of from 12 h to 48 h, more preferably from 20 to 30 h.

It is further conceivable to add seed crystals to the synthesis batches. Such an addition of seed crystals, which is well known in the art, can enhance the crystallization of zeolites and increase the crystallization rate. When used, the seed crystals may be crystals of the desired titanium zeolite, or crystals of a different titanium zeolite.

According to an embodiment of the present invention, the crystalline titanium zeolite obtained, is separated off from the reaction suspension, optionally washed and dried.

All methods known for the separation of the crystalline titanium zeolite from the suspension can be employed. Inter alia, filtration, ultra-filtration, diafiltration and centrifugation methods should be mentioned.

In case the crystalline titanium zeolite obtained is washed, said washing step can be carried out employing any suitable wash substance, such as, for example, water, alcohols, such as for example, methanol, ethanol, or methanol and propanol, or ethanol and propanol, or methanol and ethanol and propanol, or mixtures of water and at least one alcohol, such as, for example, water and ethanol or water and methanol, or water and ethanol, or eater and propanol, or water and methanol and ethanol, or water and methanol and propanol, or water and ethanol and propanol or water and ethanol and methanol and propanol. Water or a mixture of water and at least one alcohol, preferably water and ethanol, are used as wash substance.

In addition to or instead of the at least one wash process, the separated titanium zeolite can also be treated with a concentrated or diluted acid or a mixture of two or more acids.

If the titanium zeolite is subjected to washing and/or treatment with at least one acid, at least one drying step, as described below, follows according to a particularly preferred embodiment of the present invention.

Drying of the crystalline titanium zeolite is effected at temperatures, in general, in the range of from 80 to 160° C., preferably from 90 to 145° C., particularly preferably from 100 to 130° C.

Instead of the above mentioned separation methods, such as, inter alia, filtration, ultra-filtration, diafiltration and centrifugation methods, the suspension may, according to an alternative embodiment, also be subjected to spray methods, as for example spray-granulation and spray-drying.

If the separation of the crystalline titanium zeolite is carried out by means of spray method, the separating and drying step can be combined to a single step. In such case, either the reaction suspension as such or a concentrated reaction suspension can be employed. Additionally, it is possible to add a suitable additive as for example at least one suitable binder and/or at least one pore forming agent to the suspension—either to the reaction suspension as such or to the concentrated suspension—prior to spray drying or spray granulation. Suitable binders are described in detail below. As pore forming agent all pore forming agents described above can be used. In case the suspension is spray-dried, the pore forming agent—if added—may be added in two manners. First, the pore forming agent can be added to the reaction mixture prior to spray drying. However, it is also possible to add a portion of the pore forming agent to the reaction mixture prior to spray drying, with the remainder of the pore forming agent being added to the spray dried material.

In case the suspension is first concentrated to enhance the content of the titanium zeolite in the suspension, concentration can be achieved, for example, by evaporating, as for example evaporating under reduced pressure, or by cross flow filtration. Likewise, the suspension can be concentrated by separating said suspension into two fractions, wherein the solid contained in one of both fractions is separated off by filtration, diafiltration, ultrafiltration or centrifugation methods and is suspended after an optional washing step and/or drying step in the other fraction of the suspension. The thus obtained concentrated suspension can then be subjected to spray methods, as for example spray granulation and spray drying.

According to an alternative embodiment of the invention, concentration is achieved by separating the at least one titanium zeolite from the suspension, and re-suspending the titanium zeolite, optionally together with at least one suitable additive as already described above, wherein the titanium zeolite may be subjected to at least one washing step and/or at least one drying step prior to re-suspension. The re-suspended titanium zeolite can then be employed to spraying methods, preferably to spray drying.

Spray-drying is a direct method of drying slurries, suspensions or solutions by feeding a well-dispersed liquid-solid slurry, suspension or solution, often additionally containing a binder, to an atomizer and subsequently flash-drying in a stream of hot air. The atomizer can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single fluid nozzles which rely on hydrostatic pressure to force the slurry through a small nozzle. Multi-fluid nozzles are also used, where gas pressure is used to force the slurry through the nozzle. The sprayed material obtained using spray drying and spray granulation methods, like for example fluidized-bed drying, can contain solid and/or hollow spheres and can substantially consist of such spheres, which have, for example, a diameter in the range of from 5 to 500 micrometer or 5 to 300 micrometer. Single component or multiple component nozzles can be used. The use of a rotating sprayer is also conceivable. Possible inlet temperatures for the used carrier gas are, for example, in the range of from 200 to 600° C., preferably in the range of from 300 to 500° C. The outlet temperature of the carrier gas is, for example, in the range of from 50 to 200° C. Air, lean air or oxygen-nitrogen mixtures with an oxygen content of up to 10 vol.-%, preferably of up to 5 volume-%, more preferably of less than 5 volume-%, as, for example, of up to 2 volume-%, may be mentioned as carrier gases. The spray methods can be carried out in counter-current or co-current flow.

Preferably, in the context of the present invention, the titanium zeolite is separated from the reaction suspension by conventional filtration or centrifugation, optionally dried and/or calcined, and re-suspended, preferably in a mixture, preferably an aqueous mixture of at least one binder material and/or one pore-forming agent. The resulting suspension is then preferably subjected to spray-drying or spray-granulation. The obtained sprayed material may be subjected to an additional washing step, said washing step being carried out as described above. The optionally washed sprayed material is then dried and calcined wherein drying and calcination is preferably carried out as described above.

According to an alternative embodiment of the present invention, the crystallization of the titanium zeolite is effected not before the above described suspension has been spray dried. Therefore, first a suspension is formed comprising the source of silicon oxide, preferably silicon dioxide, the source of titanium oxide, and the template compound capable of forming the titanium zeolite. Then, the suspension is spray-dried, wherein subsequently, optionally additional pore forming agent is added to the spray dried titanium zeolite.

The spray dried titanium zeolite obtained according to the above mentioned processes can, optionally, be subjected to at least one wash process and/or treatment with at least one acid. If at least one wash process and/or treatment with at least one acid is carried out, preferably at least one drying step and/or at least one calcination step follows.

The at least one crystalline titanium zeolite, optionally obtained by spraying methods, can further be subjected to at least one calcination step, which is carried out according to a preferred embodiment of the invention subsequent to the drying step, or instead of the drying step. The at least one calcination step is carried out at temperatures in general in the range of from 350-750° C., preferably form 400-700° C., particularly preferably from 450-650° C.

The calcination of the crystalline titanium zeolite can be effected under any suitable gas atmosphere, wherein air and/or lean air is preferred. Furthermore, the calcinations is preferably carried out in a muffle furnace, rotary cone and/or a belt calcination furnace, wherein the calcination is generally carried out for one hour or more, for example for a time in the range of from 1 to 24 or from 4 to 12 hours. It is possible in the process according to the present invention, for example, to calcine the zeolite material once, twice or more often for in each case at least one hour, for example in each case from 4 h to 12 h, preferably from 4 h to 8 h, wherein it is possible to keep the temperatures during the calcination step constant or to change the temperatures continuously or discontinuously. If calcination is effected twice or more often, the calcination temperatures in the individual steps may be different or identical.

The titanium zeolite, prepared as described above, can be directly employed as catalyst in step (ii) or in (i) and (v).

However, it is it often desired to employ not the crystalline material per se as catalyst but the crystalline material processed to give a molding comprising the at least one titanium zeolite. Thus, according to a preferred embodiment, a molding comprising at least one titanium zeolite, as described above, is employed as catalyst.

In general, in case a molding is employed as catalyst, said catalyst may comprise all conceivable further compounds in addition to the titanium zeolite according to the invention, for example, inter alia, at least one binder and/or at least one pore forming agent. Furthermore the catalyst may comprise at least one pasting agent instead of the at least one binder and/or the at least one pore forming agent or in addition to the at least one binder and/or the at least one pore forming agent.

As binder all compounds are suitable, which provide adhesion and/or cohesion between the at least one titanium zeolite to be shaped which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these compounds. Clay minerals and naturally occurring or synthetically produced alumina, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further preferred binders are amphiphilic compounds having a polar and a nonpolar moiety and graphite. Further binders are, for example, clays, such as, for example, montmorillonites, kaolins, metakaoline, hectorite, bentonites, halloysites, dickites, nacrites or anaxites.

These binders can be used as such. It is also within the scope of the present invention to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention binders which either completely or partly comprise $SiO_2$, or which are a precursor of $SiO_2$, from which $SiO_2$ is formed in at least one further step, are very particularly preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2/g$.

Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, ValronEstersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Accordingly, the present invention also describes a catalyst containing a molding, as described above, said molding comprising a titanium zeolite as described above and additionally $SiO_2$ as binder material wherein the binder used according to (I) is a binder comprising or forming $SiO_2$.

The titanium zeolite may also be shaped without using a binder.

If desired, at least on pore forming agent can be added to the mixture of titanium zeolite and at least one binder or at least binder-precursor, for further processing and for the formation of the catalyst shaped body. Pore forming agents which may be used in the shaping process according to the invention are all compounds which, with regard to the molding produced, provide a specific pore size and/or a specific pore size distribution and/or certain pore volumes. In particular pore forming agents which provide, with regard to the molding produced, micropores and/or micropores, in particular mesopores and micropores.

As regards examples for pore forming agents which may be used, reference is made to the pore forming agents already mentioned above. Preferably, the pore forming agents used in the shaping process of the invention are polymers which are dispersible, suspendable or emulsifiable in water or in aqueous solvent mixtures. Especially preferred polymers are polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents are, for example, pulp or graphite.

If desired for the pore size distribution to be achieved, a mixture of two or more pore forming agents may be used. In a particularly preferred embodiment of the process according to the invention, as described below, the pore forming agents are removed by calcination to give the porous catalyst shaped body. Preferably, pore forming agents which provide mesopores and/or micropores, particularly preferably mesoopores, are added to the mixture of at least one binder and titanium zeolite for shaping the titanium zeolite.

The titanium zeolite can also be shaped to obtain a catalyst shaped body without using a pore forming agent.

Besides binder and optionally pore forming agent it is as well possible to add additional components, for example at least one pasting agent, to the mixture which is shaped to obtain a catalyst shaped body prior to step (i).

If at least one pasting agent is used in the process of the invention, said pasting agent is used either instead of or in addition to the at least one pore forming agent. In particular, compounds which also act as pore forming agents can be used as pasting agent. Pasting agents which may be used are all compounds known to be suitable for this purpose. These are preferably organic, in particular hydrophilic polymers, such as, for example, cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, cellulose, cellulose derivatives, water and mixtures of two or more of these compounds, such as water and cellulose or water and cellulose derivatives are used as pasting agent. In a particularly preferred embodiment of the process according to the invention, the at least one pasting agents is removed by calcination, as further described below, to give the molding.

Further, at least one acidic additive can be added to the mixture which is shaped to obtain the molding. If an acidic additive is used, organic acidic compounds which can be removed by calcination, are preferred. In this context carboxylic acids, such as, for example, formic acid, oxalic acid and/or citric acid, may be mentioned. It is also possible to use two or more of these acidic compounds.

The order of addition of the components to the mixture which is shaped to obtain the molding is not critical. If for example, a combination of a binder, a pore forming agent, a pasting agent and optionally at least one acidic compound is employed, it is possible both first to add the at least one binder then the at least one pore forming agent, the at least one acidic compound and finally the at least one pasting agent and to interchange the sequence with regard to the at least one binder, the at least one pore forming agent, the at least one acidic compound and the at least one pasting agent.

After the addition of at least one binder and/or at least one pasting agent and/or at least one pore forming agent and/or at least one acidic additive to the mixture comprising the titanium zeolite, the mixture is typically homogenized for 10 to 180 minutes. Inter alia, kneaders, edge mills or extruders are particularly preferably used for the homogenization. The mixture is preferably kneaded. On an industrial scale, grinding in an edge mill is preferred for the homogenization.

The homogenization is, as a rule, carried out at temperatures in the range of from about 10° C. to the boiling point of the pasting agent and atmospheric pressure or slightly superatmospheric pressure. Optionally, at least one of the compounds described above can then be added. The mixture thus obtained is homogenized, preferably kneaded, until an extrudable plastic material is formed.

The homogenized mixture is then shaped to obtain a molding. All known suitable shaping methods, such as extrusion, spray drying, spray granulation, briquetting, i.e. mechanical compression with or without addition of additional binder or pelleting, i.e. compacting by circular and/or rotary movements, may be employed.

Preferred shaping methods are those in which conventional extruders are employed to shape the mixture comprising the at least on titanium zeolite. Thus, for example extrudates having a diameter of from 1 to 10 mm and preferably of from 2 to 5 mm are obtained. Such extrusion apparatuses are described, for example, in "Ullmann's Enzyklopädie der Technischen Chemie", 4th edition, vol. 2, page 295 et seq., 1972. In addition to the use of an extruder, an extrusion press can also be used for the preparation of the moldings. The shape of the moldings produced according to the invention can be chosen as desired. In particular, inter alia, spheres, oval shapes, cylinders or tablets are possible. Likewise, hollow structures, as for example hollow cylinders or honeycomb formed structures or also star-shaped geometries may be mentioned.

The shaping can take place at ambient pressure or at a pressure higher than ambient pressure, for example in a pressure range of from 1 bar to several hundred bar. Furthermore, the compacting can take place at ambient temperature or at a temperature higher than ambient temperature, for example in a temperature range of from 20 to 300° C. If drying and/or calcining are part of the shaping step, temperatures of up to 600° C. are conceivable. Finally, the compacting can take place in an ambient atmosphere or in a controlled atmosphere. Controlled atmospheres are, for example, inert gas atmospheres, reducing atmospheres and/or oxidizing atmospheres.

When shaping is carried out, the shaping step is preferably followed by at least one drying step. This at least one drying step is carried out at temperatures in the range of in general from 80 to 160° C., preferably of from 90 to 145° C. and particularly preferably of from 100 to 130° C., usually for 6 h or more, for example in the range of from 6 to 24 h. However, depending on the moisture content of the material to be dried, shorter drying times, such as, for example, about 1, 2, 3, 4 or 5 h are also possible.

Before and/or after the drying step, the preferably obtained extrudate can, for example, be comminuted. Preferably granules or chips having a particle diameter of from 0.1 to 5 mm, in particular of from 0.5 to 2 mm, are obtained thereby.

According to a preferred embodiment of the present invention, the drying of the moldings, respectively, is preferably followed by at least one calcination step. Calcination is carried out at temperatures in general in the range of from 350-750° C., preferably form 400-700° C., particularly preferably from 450-650° C. The calcination can be effected under any suitable gas atmosphere, wherein air and/or lean air are preferred. Furthermore, the calcination is preferably carried out in a muffle furnace, a rotary kiln and/or a belt calcining furnace, wherein the duration of calcination is in general 1 h or more, for example in the range of from 1 to 24 h or in the range of from 3 to 12 h. In the process according to the invention, it is accordingly possible, for example, to calcine the catalyst shaped body once, twice or more often for in each case at least 1 h, such as, for example, in each case in the range of from 3 to 12 h, wherein it is possible for the temperatures during a calcination step to remain constant or to be changed continuously or discontinuously. If calcination is effected twice or more often, the calcination temperatures in the individual steps may be different or identical.

Preferably, the catalyst is subjected to a hydrothermal treatment. Hydrothermal treatment can be carried out employing any suitable method known to those skilled in the art. Thus, the catalyst or catalyst shaped in general is contacted with water or water vapor.

Typically, said hydrothermal treatment is carried out by charging the catalyst or according to the invention together with water into an autoclave, heating the slurry to a temperature in the range of from 100 to 200° C., preferably in the range of from 120 to 150° C. at a pressure in the range of from 1.5 to 5 bar, preferably in the range of from 2 to 3 bar, for a period in the range of from 1 to 48 hours, preferably in the range of from 24 to 48 hours. Typically at least one washing step, preferably with water as wash substance, follows.

After the treatment with water the catalyst is being preferably dried and/or calcined, wherein drying and calcination is carried out as already described above.

Preferably, the hydrothermal treatment is carried out by stirring the catalyst shaped body in an autoclave, wherein the stirring rate is adjusted to a stirring rate such that to avoid attrition as far as possible. If the catalyst is used in form of cylindrical extrudates, however, some attrition is desired to achieve cylindrical extrudates having rounded edges. With such extrudates having rounded edges, a higher bulk density can be achieved, for example for a possible use of the extrudates as fixed-bed catalyst in a suitable reactor such as in a tube reactor. Furthermore, the dust formation of said catalysts in the further process, thus in step (ii) and in the hydrocarbon conversion reaction, is reduced.

Epoxidation Reaction Characteristics

Regarding the oxygen selectivity of the epoxidation reaction according to (ii) or to (ii) and (v), no specific limitation exists provided it is sufficiently low. Preferably, the oxygen selectivity of the epoxidation reaction according to (ii), preferably of the epoxidation reactions according to (ii) and (v), is at most 1.2%, preferably at most 1.0%, more preferably at most 0.8%, wherein the oxygen selectivity is defined as the molar amount of oxygen comprised in the effluent stream removed in (iii), preferably the molar amount of oxygen comprised in the effluent streams removed in (iii) and (vi), relative to the molar amount of hydrogen peroxide comprised in the liquid feed stream provided in (i).

Regarding the organic by-product selectivity of the epoxidation reaction according to (ii) or to (ii) and (v), no specific limitation exists provided it is sufficiently low. Preferably, the organic by-product selectivity of the epoxidation reaction according to (ii), preferably of the epoxidation reactions according to (ii) and (v), is at most 9.0%, preferably at most 8.0%, more preferably at most 7.5%, wherein the organic by-product selectivity is defined as the molar amount of hydrogen peroxide consumed to produce the molar amount of organic by-products comprised in the effluent stream removed in (iii), preferably the molar amount of oxygen comprised in the effluent streams removed in (iii) and (vi), relative to the total molar amount of hydrogen peroxide consumed.

Catalytic System for the Epoxidation of Propylene Oxide

Further, the present invention relates to a catalytic system for the preparation of propylene oxide that can be employed in the process described above.

Preferably, such catalytic system comprises a catalyst comprising a titanium zeolite of structure type MFI and at least one potassium salt of hydroxyethylidenediphosphonic acid.

Preferably, the titanium zeolite of structure type MFI comprised in the catalyst comprising a titanium zeolite of structure type MFI comprises, preferably consists of, titanium silicalite-1.

Regarding the molar ratio of potassium relative to phosphorus in the at least one potassium salt of hydroxyethylidenediphosphonic acid in the catalytic system, no specific limitation exists. Preferably, the molar ratio of potassium relative to phosphorus in the at least one potassium salt of hydroxyethylidenediphosphonic acid is in the range of from 1:2 to 2:1, preferably from 1:2 to 1.5:1, more preferably from 0.75:1 to 1.25:1, more preferably from 0.9:1 to 1.1:1.

Preferably. according to the present invention, the at least one potassium salt of hydroxy-ethylidenediphosphonic acid is the dipotassium salt of hydroxyethylidenediphosphonic acid.

Preferably. according to the present invention, the at least one potassium salt of hydroxy-ethylidenediphosphonic acid comprises the dipotassium salt of hydroxyethylidenediphosphonic acid.

Use of the Catalytic System for the Preparation of Propylene Oxide

Further, the present invention relates to the use of the catalytic system described above for the epoxidation of propene. It also relates to the catalytic system as described above for the epoxidation of propene.

Yet further, the present invention relates to the catalytic system described above being obtainable or obtained by (i') providing a liquid feed stream comprising propene, hydrogen peroxide, methanol, water, optionally propane, and at least one dissolved potassium salt of hydroxyethylidenediphosphonic acid;

(ii') passing the liquid feed stream provided in (i') into an epoxidation reactor comprising the catalyst comprising a titanium zeolite of structure type MFI, wherein in (ii'), the liquid feed stream is preferably subjected to epoxidation reaction conditions in the epoxidation reactor, obtaining a reaction mixture comprising propylene oxide, methanol, water, and the at least one dissolved potassium salt of hydroxyethylidenediphosphonic acid, and optionally propane.

Regarding the oxygen selectivity of the catalytic system for the epoxidation reaction according to (ii'), no specific limitation exists. Preferably, the catalytic system exhibits and oxygen selectivity for the epoxidation reaction according to (ii') of at most 1.2%, preferably at most 1.0%, more preferably at most 0.8%, wherein the oxygen selectivity is defined as the molar amount of oxygen comprised in the effluent stream removed in (iii), preferably the molar amount of oxygen comprised in the effluent streams removed in (iii) and (vi), relative to the molar amount of hydrogen peroxide comprised in the liquid feed stream provided in (i').

Regarding the organic by-product selectivity of the catalytic system for the epoxidation reaction according to (ii'), no specific limitation exists. Preferably, the catalytic system exhibits an organic by-product selectivity of the epoxidation reaction according to (ii') of at most 9.0%, preferably at most 8.0%, more preferably at most 7.5%, wherein the organic by-product selectivity is defined as the molar amount of hydrogen peroxide consumed to produce the molar amount of organic by-products comprised in the effluent stream removed in (iii), preferably the molar amount of oxygen comprised in the effluent streams removed in (iii) and (vi), relative to the total molar amount of hydrogen peroxide consumed.

Use of Hydroxyethylidenediphosphonic Acid

Further, the present invention relates to the use of at least one potassium salt of hydroxyethylidenediphosphonic acid as an additive for a titanium zeolite of framework structure type MFI in a preferably continuous process for the preparation of propylene oxide.

Regarding the solvent in the process for the preparation of propylene oxide, no specific limitation exists, provided propene is epoxidized to propylene oxide. Preferably, the solvent in the process for the preparation of propylene oxide is methanol.

Regarding the epoxidation agent in the process for the preparation of propylene oxide, no specific limitation exists, provided propene is epoxidized to propylene oxide. Preferably, the epoxidation agent in the process for the preparation of propylene oxide is hydrogen peroxide.

Preferably, according to the present invention, no potassium salt of phosphoric acid, preferably no alkali salt of phosphoric acid, more preferably no salt of phosphoric acid is employed as an additive for a titanium zeolite of framework structure type MFI in addition to the at least one potassium salt of hydroxyethylidenediphosphonic acid.

Thus, preferably according to the present invention, the at least one potassium salt of hydroxyethylidenediphosphonic acid is the sole additive for the titanium zeolite of framework structure type MFI.

Regarding the molar ratio of potassium relative to phosphorus in the at least one potassium salt of hydroxyethylidenediphosphonic acid, no specific limitation exists. Preferably, the molar ratio of potassium relative to phosphorus in the at least one potassium salt of hydroxy-ethylidenediphosphonic acid is in the range of from 1:2 to 2:1, preferably from 1:2 to 1.5:1, more preferably from 0.75:1 to 1.25:1, more preferably from 0.9:1 to 1.1:1.

Thus, preferably according to the present invention, the at least one potassium salt of hydroxyethylidenediphosphonic acid comprises the dipotassium salt of hydroxyethylidenediphosphonic acid.

Preferably according to the present invention, the at least one potassium salt of hydroxy-ethylidenediphosphonic acid is the dipotassium salt of hydroxyethylidene-diphosphonic acid.

Liquid Stream Composition

Yet further, the present invention relates to a liquid stream, of which from 99 to 100 weight-% consists of propene, hydrogen peroxide, methanol, water, at least one dissolved potassium salt of hydroxyethylidenediphosphonic acid, and optionally propane, said liquid stream having a solids content of at most 100 weight-ppb, preferably at most 30 weight-ppb at a temperature in the range of from 25 to 50° C. and a pressure in the range of from 15 to 25 bar.

The present invention is further illustrated by the following embodiments and combinations of embodiments as indicated by the respective dependencies and references.

1. A continuous process for the preparation of propylene oxide, comprising
   (i) providing a liquid feed stream comprising propene, hydrogen peroxide, methanol, water, at least one dissolved potassium salt of hydroxyethylidenediphosphonic acid, and optionally propane;
   (ii) passing the liquid feed stream provided in (i) into an epoxidation reactor comprising a catalyst comprising a titanium zeolite of structure type MFI, and subjecting the liquid feed stream to epoxidation reaction conditions in the epoxidation reactor, obtaining a reaction mixture comprising propylene oxide, methanol, water, and the at least one dissolved potassium salt of hydroxyethylidenediphosphonic acid, and optionally propane;
   (iii) removing an effluent stream from the epoxidation reactor, the effluent stream comprising propylene oxide, methanol, water, at least a portion of the at least one potassium salt of hydroxyethylidenediphosphonic acid, and optionally propane.

2. The process of embodiment 1, wherein the molar ratio of potassium relative to phosphorus in the at least one potassium salt of hydroxyethylidenediphosphonic acid is in the range of from 1:2 to 2:1, preferably from 1:2 to 1.5:1, more preferably from 0.75:1 to 1.25:1, more preferably from 0.9:1 to 1.1:1.

3. The process of any of embodiments 1 to 2, wherein the at least one potassium salt of hydroxyethylidenediphosphonic acid comprises the dipotassium salt of hydroxyethylidenediphosphonic acid.

4. The process of any of embodiments 1 to 2, wherein the at least one potassium salt of hydroxyethylidenediphosphonic acid is the dipotassium salt of hydroxyethylidenediphosphonic acid.

5. The process of any of embodiments 1 to 4, wherein the liquid feed stream provided in (i) comprises the dipotassium salt of hydroxyethylidenediphosphonic acid as the at least one dissolved potassium salt of hydroxyethylidenediphosphonic acid.

6. The process of any of embodiments 1 to 5, wherein in the liquid feed stream provided in (i), the molar ratio of the potassium comprised in the at least one potassium salt of hydroxyethylidenediphosphonic acid relative to the hydrogen peroxide is in the range of from $5\times10^{-6}$:1 to $1000\times10^{-6}$:1, preferably from $10\times10^{-6}$:1 to $700\times10^{-6}$:1, more preferably from $10\times10^{-6}$:1 to $500\times10^{-6}$:1.

7. The process of any of embodiments 1 to 6, wherein in the liquid feed stream provided in (i), the molar ratio of the potassium relative to the the potassium comprised in the at least one potassium salt of hydroxyethylidenediphosphonic acid is in the range of from 1.2:1 to 1:1, preferably from 1.1:1 to 1:1, more preferably from 1.05:1 to 1:1.

8. The process of any of embodiments 1 to 7, wherein in the liquid feed stream provided in (i), the amount of potassium not derived from the at least one potassium salt of hydroxyethylidenediphosphonic acid is less that 100 weight-ppm, preferably less than 10 weight-ppm, more preferably less than 1 weight-ppm based on the total weight of the liquid feed stream.

9. The process of any of embodiments 1 to 8, wherein in the liquid feed stream provided in (i), the molar ratio of the phosphorus relative to the phosphorus comprised in the at least one potassium salt of hydroxyethylidenediphosphonic acid is in the range of from 1.2:1 to 1:1, preferably from 1.1:1 to 1:1, more preferably from 1.05:1 to 1:1.

10. The process of any of embodiments 1 to 9, wherein in the liquid feed stream provided in (i), the amount of phosphorus not derived from the at least one potassium salt of hydroxyethylidenediphosphonic acid is less that 100 weight-ppm, preferably less than 10 weight-ppm, more preferably less than 1 weight-ppm based on the total weight of the liquid feed stream.

11. The process of any of embodiments 1 to 10, wherein in the liquid feed stream provided in (i), the molar ratio of sodium relative to hydrogen peroxide is in the range of from $1\times10^{-6}$:1 to $250\times10^{-6}$:1, preferably from $5\times10^{-6}$:1 to $50\times10^{-6}$:1.

12. The process of any of embodiments 1 to 11, wherein in the liquid feed stream provided in (i), ammonium $NH_4^+$ is comprised in an amount of at most 2 weight-ppm, preferably at most 1 weight-ppm, based on the total weight of the liquid feed stream.

13. The process of any of embodiments 1 to 12, wherein at least 95 weight-%, preferably from 95 to 100 weight-%, more preferably from 98 to 100 weight-%, more preferably from 99 to 100 weight-% of the liquid feed stream provided in (i) consists of the propene, the hydrogen peroxide, the methanol, the water, the at least one dissolved potassium salt of hydroxyethylidenediphosphonic acid, and optionally propane.

14. The process of any of embodiments 1 to 13, wherein in (i), the liquid feed stream is provided by combining a stream comprising hydrogen peroxide and optionally water, a stream comprising methanol and optionally water, and a stream comprising propene and optionally propane, and wherein prior to combining these streams, an aqueous stream comprising the at least one dissolved potassium salt of hydroxyethylidenediphosphonic acid is admixed either with the stream comprising hydrogen peroxide and optionally water, or with the stream comprising methanol and optionally water, or with the stream comprising propene and optionally propane, or with a mixed stream of two or three of these streams.

15. The process of any of embodiments 1 to 14, wherein in (i), the liquid feed stream is provided by combining a stream comprising hydrogen peroxide and optionally water, a stream comprising methanol and optionally water, and a stream comprising propene and optionally propane, and wherein prior to combining these streams, an aqueous stream comprising the at least one dissolved potassium salt of hydroxyethylidenediphosphonic acid is admixed with the stream comprising hydrogen peroxide and optionally water, or with the stream comprising methanol and optionally water, or with a mixed stream thereof.

16. The process of embodiment 15, wherein the concentration of the at least one potassium salt of hydroxyethylidenediphosphonic acid in the aqueous stream comprising the at least one potassium salt of hydroxyethylidenediphosphonic acid is in the range of from 0.1 to 50 weight %, preferably from 0.2 to 45 weight %, more preferably from 0.5 to 40 weight % based on the total weight of the aqueous stream comprising the at least one potassium salt of hydroxyethylidenediphosphonic acid.

17. The process of any of embodiments 14 to 16, wherein the stream comprising hydrogen peroxide and optionally water is an aqueous hydrogen peroxide stream having a hydrogen peroxide concentration in the range of from 25 to 75 weight-%, preferably from 30 to 50 weight-%, based on the total weight of the aqueous hydrogen peroxide stream.

18. The process of any of embodiments 14 to 17, wherein the aqueous hydrogen peroxide stream further comprises sodium with a molar ratio of sodium relative to hydrogen peroxide in the range of from $1\times10^{-6}$:1 to $250\times10^{-6}$, preferably from $5\times10^{-6}$:1 to $50\times10^{-6}$:1.

19. The process of any of embodiments 1 to 18, wherein the liquid feed stream passed into the epoxidation reactor in (ii) has a temperature in the range of from 0 to 60° C., preferably from 25 to 50° C.

20. The process of any of embodiments 1 to 19, wherein the liquid feed stream passed into the epoxidation reactor in (ii) is at a pressure in the range of from 14 to 100 bar, preferably from 15 to 25 bar.

21. The process of any of embodiments 1 to 20, wherein in (ii), the temperature of the reaction mixture is controlled using a heat transfer medium, preferably by passing the heat transfer medium through a jacket of the epoxidation reactor.

22. The process of embodiment 21, wherein in (ii), the epoxidation conditions comprise an epoxidation reaction temperature in the range of from 10 to 100° C., preferably from 30 to 80° C., more preferably from 40 to 65° C., wherein the epoxidation reaction temperature is defined as the temperature of the heat transfer medium prior to controlling of the temperature of the reaction mixture, preferably as the temperature of the heat transfer medium at the entrance of the jacket of the epoxidation reactor.

23. The process of any of embodiments 1 to 22, wherein in (ii), the epoxidation conditions comprise an epoxidation reaction pressure in the range of from 14 to 100 bar, preferably from 15 to 32 bar, more preferably from 15 to 25 bar, wherein the epoxidation reaction pressure is defined as the pressure at the exit of the epoxidation reactor.

24. The process of any of embodiments 1 to 23, wherein in (ii), the epoxidation conditions comprise a catalyst loading in the range of from 0.05 to 1.25 $h^{-1}$, preferably from 0.1 to 1 $h^{-1}$, more preferably from 0.2 to 0.7 $h^{-1}$, wherein the catalyst loading is defined as the ratio of the mass flow rate in kg/h of hydrogen peroxide contained in liquid feed stream provided in (i) divided by the amount in kg of catalyst comprising a titanium zeolite of structure type MFI comprised in the epoxidation reactor in (ii).

25. The process of any of embodiments 1 to 24, wherein the effluent stream removed in (iii) additionally comprises hydrogen peroxide and optionally propene, the process further comprising
   (iv) separating propylene oxide from the effluent stream, obtaining a stream being depleted in propylene oxide and comprising hydrogen peroxide, methanol, water, at least a portion of the at least one potassium salt of hydroxyethylidenediphosphonic acid optionally propene and optionally propane;
   (v) passing the stream being depleted in propylene oxide and comprising hydrogen peroxide, methanol, water, at least a portion of the at least one potassium salt of hydroxyethylidenediphosphonic acid optionally propene and optionally propane obtained in (iv) into an epoxidation reactor comprising a catalyst comprising a titanium zeolite of structure type MFI, and subjecting the stream to epoxidation reaction conditions in the epoxidation reactor, obtaining a reaction mixture comprising propylene oxide, methanol, water, the portion of the at least one dissolved potassium salt of hydroxyethylidenediphosphonic acid, and optionally propane;
   (vi) removing an effluent stream from the epoxidation reactor, the effluent stream comprising propylene oxide, methanol, water, at least a portion of the portion of the at least one potassium salt of hydroxyethylidenediphosphonic acid, and optionally propane.
26. The process of embodiment 25, wherein the separating in (iv) is carried out by rectifying, preferably by distilling.
27. The process of embodiment 26, wherein the distilling is carried out in a distillation tower.
28. The process of any of embodiments 25 to 27, wherein in (v), the epoxidation conditions comprise adiabatic epoxidation reactions.
29. The process of any of embodiments 25 to 28, wherein in (v), the epoxidation conditions comprise a catalyst loading in the range of from 0.01 to 0.2 $h^{-1}$, preferably of from 0.015 to 0.15 $h^{-1}$, more preferably of from 0.03 to 0.1 $h^{-1}$, wherein the catalyst loading is defined as the ratio of the mass flow rate in kg/h of hydrogen peroxide contained in the stream stream being depleted in propylene oxide and comprising hydrogen peroxide, methanol, water, at least a portion of the at least one potassium salt of hydroxyethylidenediphosphonic acid optionally propene and optionally propane obtained in (iv) divided by the amount in kg of catalyst comprising a titanium zeolite of structure type MFI comprised in the epoxidation reactor in (v).
30. The process of any of embodiments 1 to 29, wherein the epoxidation conditions comprise a hydrogen peroxide conversion in the range of from 90 to 100%, preferably from 95 to 100%, more preferably from 99 to 100%, wherein the hydrogen peroxide conversion is calculated based on the amount of hydrogen peroxide comprised in the effluent stream removed in (iii), preferably in (vi), relative to the amount of hydrogen peroxide comprised in the liquid feed stream provided in (i).
31. The process of any of embodiments 1 to 30, wherein in (ii), preferably in (ii) and (v), the catalyst comprising a titanium zeolite of structure type MFI is present in the reactor as fixed-bed catalyst.
32. The process of any of embodiments 1 to 31, wherein in (ii), preferably in (ii) and (v), the titanium zeolite of structure type MFI comprised in the catalyst comprising a titanium zeolite of structure type MFI comprises, preferably consists of, titanium silicalite-1.
33. The process of any of embodiments 1 to 32, wherein the oxygen selectivity of the epoxidation reaction according to (ii), preferably of the epoxidation reactions according to (ii) and (v), is at most 1.2%, preferably at most 1.0%, more preferably at most 0.8%, wherein the oxygen selectivity is defined as the molar amount of oxygen comprised in the effluent stream removed in (iii), preferably the molar amount of oxygen comprised in the effluent streams removed in (iii) and (vi), relative to the molar amount of hydrogen peroxide comprised in the liquid feed stream provided in (i).
34. The process of any of embodiments 1 to 33, wherein the organic by-product selectivity of the epoxidation reaction according to (ii), preferably of the epoxidation reactions according to (ii) and (v), is at most 9.0%, preferably at most 8.0%, more preferably at most 7.5%, wherein the organic by-product selectivity is defined as the molar amount of hydrogen peroxide consumed to produce the molar amount of organic by-products comprised in the effluent stream removed in (iii), preferably the molar amount of oxygen comprised in the effluent streams removed in (iii) and (vi), relative to the total molar amount of hydrogen peroxide consumed.
35. A catalytic system comprising a catalyst comprising a titanium zeolite of structure type MFI and at least one potassium salt of hydroxyethylidenediphosphonic acid.
36. The catalytic system of embodiment 35, wherein the titanium zeolite of structure type MFI comprised in the catalyst comprising a titanium zeolite of structure type MFI comprises, preferably consists of, titanium silicalite-1.
37. The catalytic system of any of embodiments 35 or 36, wherein the molar ratio of potassium relative to phosphorus in the at least one potassium salt of hydroxyethylidenediphosphonic acid is in the range of from 1:2 to 2:1, preferably from 1:2 to 1.5:1, more preferably from 0.75:1 to 1.25:1, more preferably from 0.9:1 to 1.1:1.
38. The catalytic system of any of embodiments 35 to 37, wherein the at least one potassium salt of hydroxyethylidenediphosphonic acid is the dipotassium salt of hydroxyethylidenediphosphonic acid.
39. The catalytic system of any of embodiments 35 to 38, wherein the at least one potassium salt of hydroxyethylidenediphosphonic acid comprises the dipotassium salt of hydroxyethylidenediphosphonic acid.
40. Use of the catalytic system of any of embodiments 35 to 39 for the epoxidation of propene.
41. The catalytic system of any of embodiments 35 to 40 for the epoxidation of propene.
42. The catalytic system of any of embodiments 35 to 41, being obtainable or obtained by
   (i') providing a liquid feed stream comprising propene, hydrogen peroxide, methanol, water, optionally propane, and at least one dissolved potassium salt of hydroxyethylidenediphosphonic acid;
   (ii') passing the liquid feed stream provided in (i') into an epoxidation reactor comprising the catalyst comprising a titanium zeolite of structure type MFI, wherein in (ii'), the liquid feed stream is preferably subjected to epoxidation reaction conditions in the epoxidation reactor, obtaining a reaction mixture comprising propylene oxide, methanol, water, and the at least one dissolved potassium salt of hydroxyethylidenediphosphonic acid, and optionally propane.
43. The catalytic system of any of embodiments 35 to 42, exhibiting an oxygen selectivity for the epoxidation reaction according to (ii') of at most 1.2%, preferably at most 1.0%, more preferably at most 0.8%, wherein the oxygen selectivity is defined as the molar amount of oxygen comprised in the effluent stream removed in (iii), preferably the molar amount of oxygen comprised in the effluent streams removed in (iii) and (vi), relative to the molar amount of hydrogen peroxide comprised in the liquid feed stream provided in (i).

44. The catalytic system of any of embodiments 35 to 43, exhibiting an organic by-product selectivity of the epoxidation reaction according to (ii') of at most 9.0%, preferably at most 8.0%, more preferably at most 7.5%, wherein the organic by-product selectivity is defined as the molar amount of hydrogen peroxide consumed to produce the molar amount of organic by-products comprised in the effluent stream removed in (iii), preferably the molar amount of oxygen comprised in the effluent streams removed in (iii) and (vi), relative to the total molar amount of hydrogen peroxide consumed.

45. Use of at least one potassium salt of hydroxyethylidenediphosphonic acid as an additive for a titanium zeolite of framework structure type MFI in a preferably continuous process for the preparation of propylene oxide.

46. The use of embodiment 45, wherein the solvent in the process for the preparation of propylene oxide is methanol.

47. The use of embodiment 45 or 46, wherein the epoxidation agent in the process for the preparation of propylene oxide is hydrogen peroxide.

48. The use of any of embodiments 45 to 47, wherein no potassium salt of phosphoric acid, preferably no alkali salt of phosphoric acid, more preferably no salt of phosphoric acid is employed as an additive for a titanium zeolite of framework structure type MFI in addition to the at least one potassium salt of hydroxyethylidenediphosphonic acid.

49. The use of any of embodiments 45 to 48, wherein the at least one potassium salt of hydroxyethylidenediphosphonic acid is the sole additive for the titanium zeolite of framework structure type MFI.

50. The use of any of embodiments 45 to 49, wherein the molar ratio of potassium relative to phosphorus in the at least one potassium salt of hydroxyethylidenediphosphonic acid is in the range of from 1:2 to 2:1, preferably from 1:2 to 1.5:1, more preferably from 0.75:1 to 1.25:1, more preferably from 0.9:1 to 1.1:1.

51. The use of any of embodiments 45 to 50, wherein the at least one potassium salt of hydroxyethylidenediphosphonic acid comprises the dipotassium salt of hydroxyethylidenediphosphonic acid.

52. The use of any of embodiments 45 to 51, wherein the at least one potassium salt of hydroxyethylidenediphosphonic acid is the dipotassium salt of hydroxyethylidenediphosphonic acid.

53. A liquid stream, of which from 99 to 100 weight-% consists of propene, hydrogen peroxide, methanol, water, at least one dissolved potassium salt of hydroxy-ethylidenediphosphonic acid, and optionally propane, said liquid stream having a solids content of at most 100 ppb, preferably at most 30 ppb at a temperature in the range of from 25 to 50° C. and a pressure in the range of from 15 to 25 bar.

The present invention is further illustrated by the following examples.

EXAMPLES

Reference Example 1: Preparation of a Titanium Containing Zeolite (TS-1)

In a reaction vessel, 550 kg DI water were provided and stirred. 400 kg TPAOH (tetra-n-propylammonium hydroxide) were added under stirring. Stirring was continued for 1 h. The resulting mixture was transferred in a suitable vessel. The reaction vessel was washed twice with 2000 l DI water in total. In the washed reaction vessel, 300 kg TEOS (tetraethoxysilane) were provided and stirred. A mixture of 80 kg TEOS and 16 kg TEOT (tetraethyl orthotitanate) was added to the 300 kg TEOS. The remaining 340 kg TEOS were added.

Subsequently, the TPAOH solution was added, and the resulting mixture was stirred for another hour. Then, the reaction vessel was heated and the ethanol obtained was separated by distillation. When the internal temperature of the vessel had reached 95° C., the reaction vessel was cooled. 1143 kg water were added to the resulting suspension in the vessel, and the mixture was stirred for another hour. Crystallization was performed at 175° C. within 24 h at autogenous pressure. The obtained titanium silicalite-1 crystals were separated, dried, and calcined at a temperature of 500° C. in air.

The obtained powder and Walocel® were mixed in a muller and mixed for 5 min. Within 10 min, the polystyrene dispersion was continuously added. Subsequently, 15 l Ludox® AS-40 were continuously added. The resulting mixture was mixed for 5 min, and polyethylene oxide was continuously added within 15 min, followed by mixing for 10 min. Then, water was added. The formable mass was extruded through a matrix having circular holes with a diameter of 1.5 mm. The obtained strands were dried in a band drier at a temperature of 120° C. for 2 h and calcined at a temperature of 550° C. in lean air (100 m$^3$/h air/100 m$^3$/h nitrogen). The yield was 89 kg extrudates.

For the subsequent water treatment of the extrudates, 880 kg DI water were filled in a respective stirred vessel, and the extrudates were added. At a pressure of 84 mbar, the vessel was heated to an internal temperature of from 139 to 143° C. The resulting pressure was in the range of from 2.1 to 2.5 bar. Water treatment was carried out for 36 h. The extrudates were separated by filtration, dried for 16 h at 123° C. in air, heated to a temperature of 470° C. with 2° C./min and kept at a temperature of 490° C. in air for 5 h. The yield was 81.2 kg.

Reference Example 2: Experimental Setup for Example 1 and Comparative Example 1

A TS-1 catalyst as obtained according to Reference Example 1 above was loaded into a reaction tube with a length of 180 cm and a volume of 300 ml. The tube diameter was 0.75 inch (1.905 cm), with a wall thickness of 0.07 inch (0.19 cm). In the center of the reaction tube a smaller (0.125 inch (0.3175 cm)) tube was installed, containing the thermoelements for measuring the temperature over the catalyst bed.

Feed-materials: 54 g/h Propene (liquid)
  94 g/h 40% $H_2O_2$
Solvent: 390 g/h Methanol
Buffer-solution: 4-8 g/h 0.3 weight-% $K_2HPO_4$/$K_2HEDP$
  (flow adjusted to maintain 130-238 micromole $K^+$/(mole $H_2O_2$))

Propene was stored in 50 l gas bottles, containing dip tubes, facilitating the transfer to the mini-plant by means of 25 bar nitrogen pressure. The precise amount was measured using a Brunkhorst flow meter with a 0-500 g/h range and the flow is controlled by means of a Flowserve control-valve. Hydrogen peroxide was transferred into the reactor using a Grundfos pump DME2. The amount was determined using a balance. The measurement showed liters/minute. The respective buffer solution was fed to the reactor, using an HPLC pump. The precise amount was determined using a balance. For feeding the methanol a Lewa pump with a range of 0-1500 ml/h was used. Feed control was accomplished using a Lewa KMM. Nitrogen was fed using a Flowserve control-valve. The amount was measured using a Brunkhorst flow meter with a range of 0-200 Nl/h.

The experiments were carried out at an absolute pressure of 20 bar. The temperature in the reactor was controlled to ensure a $H_2O_2$ conversion of approximately 90%. Typical start temperature was approximately 43° C. Then the temperature was slowly ramped up to approximately 60° C. final over a run-time of 600 hours. At the beginning of the run the reactor was cooled as the exothermic heat would overheat the reactor otherwise. Towards the end of the run the reactor was heated to reach a temperature of 60° C. All feed-materials were entering the reactor tube via a 0.25 inch (0.635 cm)-mixer. Feed direction was bottom to top.

The reactor effluent was passed through a 2 micrometer filter to remove fine (catalyst) particles before it was passed into the first separator. The bottom level valve controlled a level of 25% in the first separator, while the upper pressure valve set a pressure of 20 bars over the entire upstream reaction system. The second separator was also operated at a liquid level of 25%, while the upper pressure valve reduced the pressure to 2 bars.

This lower pressure served for allowing the flashing of unconverted propene, allowing a safe sample taking, and having an additional safety buffer. The two separators had a volume of 2 liters each and were kept at a temperature of 5° C., using cooling water. A nitrogen stream of 5 Nl/h was fed through the entire system (reactor→$1^{st}$ separator-$2^{nd}$ separator→vent-system) to maintain a sufficient gas flow in the direction of the vent to ascertain that traces of oxygen, formed by partial decomposition of $H_2O_2$ were flashed out and could be analyzed at the end of the vent pipe.

Example 1: Using HEDP as Buffer

As a buffer, the di-potassium salt of hydroxyethane diphosphonic acid ($K_2$HEDP (the trade name of the material is Dequest® 2014 from Italmatch)) was used:

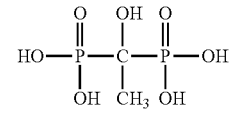

(1-hydroxyethane-1,1-diyl)bis(phosphonic acid)

At the first 620 hours on-stream time, a $K_2$HEDP concentration of 208 micromole $K^+$/mole-$H_2O_2$ was adjusted, and then reduced to 138 micromole $K^+$/mole-$H_2O_2$. The following results were obtained (see Table 1 below):

TABLE 1

Results of Example 1

| Time [h] | T [° C.] | X-HP [%] | S-PO [%] | AA [%] | PM2 [%] | PM1 [%] | Ac [%] | PG [%] | $O_2$ [%] |
|---|---|---|---|---|---|---|---|---|---|
| 23 | 43 | 98.6 | 94.6 | 0.41 | 2.09 | 2.09 | 0.14 | 0.72 | 0.1 |
| 47 | 43 | 93.2 | 96.1 | 0.43 | 1.30 | 1.36 | 0.14 | 0.66 | 0.2 |
| 71 | 43 | 94.3 | 96.0 | 0.44 | 1.38 | 1.40 | 0.22 | 0.58 | 0.2 |
| 95 | 43 | 93.2 | 95.6 | 0.55 | 1.49 | 1.43 | 0.31 | 0.57 | 0.25 |
| 119 | 44 | 92.6 | 95.6 | 0.57 | 1.47 | 1.44 | 0.29 | 0.59 | 0.25 |
| 143 | 44 | 92.6 | 95.6 | 0.54 | 1.56 | 1.47 | 0.26 | 0.53 | 0.25 |
| 167 | 44 | 89.9 | 95.6 | 0.58 | 1.48 | 1.45 | 0.35 | 0.56 | 0.3 |
| 191 | 45 | 90.6 | 96.0 | 0.65 | 1.29 | 1.23 | 0.40 | 0.47 | 0.3 |
| 215 | 47 | 90.5 | 95.7 | 0.64 | 1.35 | 1.35 | 0.41 | 0.52 | 0.3 |
| 239 | 47 | 83.0 | 96.1 | 0.59 | 1.21 | 1.18 | 0.45 | 0.48 | 0.3 |
| 263 | 49 | 85.1 | 95.8 | 0.66 | 1.30 | 1.24 | 0.49 | 0.51 | 0.3 |
| 287 | 51 | 89.0 | 95.5 | 0.72 | 1.37 | 1.37 | 0.43 | 0.57 | 0.35 |
| 311 | 51 | 90.6 | 95.3 | 0.78 | 1.47 | 1.44 | 0.43 | 0.57 | 0.4 |
| 335 | 51 | 92.6 | 95.0 | 1.01 | 1.57 | 1.51 | 0.41 | 0.53 | 0.35 |
| 359 | 51 | 91.2 | 95.0 | 1.20 | 1.42 | 1.36 | 0.47 | 0.54 | 0.35 |
| 383 | 51 | 86.6 | 94.8 | 1.19 | 1.43 | 1.49 | 0.47 | 0.60 | 0.4 |
| 407 | 53 | 88.8 | 94.4 | 1.19 | 1.58 | 1.62 | 0.51 | 0.65 | 0.45 |
| 431 | 53 | 88.4 | 94.2 | 1.31 | 1.62 | 1.65 | 0.57 | 0.68 | 0.5 |
| 455 | 54 | 89.5 | 94.3 | 1.29 | 1.60 | 1.61 | 0.56 | 0.67 | 0.55 |
| 479 | 55 | 87.2 | 94.2 | 1.28 | 1.63 | 1.56 | 0.59 | 0.69 | 0.55 |
| 503 | 57 | 88.1 | 94.4 | 1.23 | 1.57 | 1.54 | 0.57 | 0.68 | 0.6 |
| 527 | 58 | 89.2 | 94.4 | 1.20 | 1.58 | 1.53 | 0.55 | 0.70 | 0.6 |
| 551 | 58 | 89.2 | 94.4 | 1.24 | 1.56 | 1.49 | 0.60 | 0.69 | 0.65 |
| 575 | 58 | 92.6 | 94.2 | 1.21 | 1.63 | 1.69 | 0.58 | 0.73 | 0.7 |
| 599 | 58 | 92.1 | 93.9 | 1.26 | 1.74 | 1.77 | 0.59 | 0.78 | 0.75 |
| 623 | 58 | 89.2 | 93.8 | 1.24 | 1.78 | 1.76 | 0.60 | 0.79 | 0.8 |
| 647 | 58 | 91.9 | 92.0 | 1.42 | 2.22 | 2.57 | 0.69 | 1.06 | 0.6 |
| 671 | 58 | 91.9 | 91.4 | 1.44 | 2.54 | 2.81 | 0.65 | 1.21 | 0.6 |
| 695 | 58 | 91.8 | 91.1 | 1.43 | 2.64 | 2.89 | 0.65 | 1.25 | 0.65 |

Time Length of catalyst cycle/on-stream time in hours
T [° C.] Cooling water temperature in degree Celsius
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
$O_2$ [%] Selectivity to oxygen in mole-% due to hydrogen peroxide decomposition
HEDP Hydroxyethane diphosphonic acid
DKP Di-potassium-phosphate $K_2HPO_4$
$K_2$HEDP Di-potassium salt of HEDP Comparative Example 1: Using $K_2HPO_4$ as Buffer The following results were obtained (see Table 2 below):

TABLE 2

Results of Comparative Example 1

| Time [h] | T [° C.] | X-HP [%] | S-PO [%] | AA [%] | PM2 [%] | PM1 [%] | Ac [%] | PG [%] | $O_2$ [%] |
|---|---|---|---|---|---|---|---|---|---|
| 23 | 43 | 97.3 | 94.3 | 0.45 | 2.19 | 2.14 | 0.26 | 0.67 | 0.1 |
| 47 | 44 | 89.2 | 95.8 | 0.54 | 1.51 | 1.37 | 0.32 | 0.47 | 0.15 |
| 71 | 46 | 86.5 | 95.7 | 0.55 | 1.55 | 1.42 | 0.32 | 0.50 | 0.2 |
| 95 | 48 | 87.9 | 95.5 | 0.58 | 1.60 | 1.48 | 0.32 | 0.55 | 0.25 |
| 119 | 50 | 91.2 | 95.4 | 0.60 | 1.62 | 1.51 | 0.30 | 0.59 | 0.3 |
| 143 | 50 | 91.2 | 95.2 | 0.64 | 1.65 | 1.62 | 0.31 | 0.60 | 0.3 |
| 167 | 50 | 89.7 | 95.0 | 0.66 | 1.68 | 1.68 | 0.34 | 0.67 | 0.35 |
| 191 | 51 | 91.9 | 94.8 | 0.68 | 1.76 | 1.69 | 0.37 | 0.68 | 0.35 |
| 215 | 52 | 90.8 | 95.0 | 0.70 | 1.62 | 1.65 | 0.36 | 0.71 | 0.35 |
| 239 | 52 | 91.5 | 94.7 | 0.72 | 1.74 | 1.73 | 0.40 | 0.69 | 0.35 |
| 263 | 52 | 88.9 | 95.0 | 0.74 | 1.63 | 1.58 | 0.44 | 0.65 | 0.35 |
| 287 | 54 | 89.5 | 94.9 | 0.76 | 1.63 | 1.55 | 0.47 | 0.66 | 0.4 |
| 311 | 54 | 90.3 | 94.5 | 1.24 | 1.63 | 1.55 | 0.40 | 0.63 | 0.4 |
| 335 | 54 | 91.2 | 94.4 | 1.14 | 1.70 | 1.69 | 0.44 | 0.65 | 0.4 |
| 359 | 52 | 90.8 | 94.2 | 1.29 | 1.68 | 1.68 | 0.47 | 0.69 | 0.4 |
| 383 | 55 | 89.2 | 94.2 | 1.32 | 1.68 | 1.65 | 0.49 | 0.68 | 0.45 |
| 407 | 56 | 93.0 | 93.4 | 1.43 | 1.88 | 1.95 | 0.53 | 0.79 | 0.5 |
| 431 | 56 | 91.1 | 93.4 | 1.36 | 1.91 | 1.98 | 0.57 | 0.81 | 0.55 |
| 455 | 56 | 89.2 | 93.4 | 1.39 | 1.93 | 1.90 | 0.62 | 0.79 | 0.6 |
| 479 | 57 | 89.4 | 93.1 | 1.44 | 1.92 | 2.00 | 0.63 | 0.86 | 0.6 |
| 503 | 58 | 88.3 | 93.2 | 1.34 | 1.94 | 1.97 | 0.66 | 0.93 | 0.6 |
| 527 | 59 | 89.5 | 93.1 | 1.34 | 1.97 | 1.97 | 0.67 | 0.93 | 0.7 |
| 551 | 59 | 89.9 | 93.2 | 1.34 | 1.92 | 1.97 | 0.68 | 0.89 | 0.7 |
| 575 | 59 | 90.5 | 92.9 | 1.40 | 1.99 | 2.02 | 0.72 | 0.92 | 0.75 |
| 599 | 59 | 90.5 | 92.8 | 1.46 | 2.04 | 2.02 | 0.72 | 0.92 | 0.8 |
| 623 | 59 | 88.9 | 92.7 | 1.53 | 2.12 | 2.06 | 0.68 | 0.93 | 0.8 |
| 647 | 60 | 90.3 | 92.7 | 1.53 | 2.12 | 2.04 | 0.71 | 0.91 | 0.85 |
| 671 | 60 | 89.9 | 92.5 | 1.57 | 2.18 | 2.06 | 0.73 | 0.92 | 0.9 |
| 695 | 61 | 91.2 | 92.5 | 1.62 | 2.18 | 2.06 | 0.73 | 0.94 | 0.95 |

Time Length of catalyst cycle/on-stream time in hours
T [° C.] Cooling water temperature in degree Celsius
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
$O_2$ [%] Selectivity to oxygen in mole-% due to hydrogen peroxide decomposition
HEDP Hydroxyethane diphosphonic acid
DKP Di-potassium-phosphate $K_2HPO_4$
$K_2HEDP$ Di-potassium salt of HEDP Results of Example 1 and Comparative Example 1

The graphs according to FIGS. 1 to 5 clearly illustrate the advantage of using $K_2HEDP$ in comparison with the standard buffer $K_2HPO_4$ in terms of decreased by-product selectivities and increased main product PO selectivity as well as extended catalyst activity/lower deactivation based on the cooling water temperature required to maintain a conversion of $H_2O_2$ of about 90%.

Reference Example 3: Experimental Setup for Example 2

A TS-1 catalyst as obtained according to Reference Example 1 above (3497 g) was loaded into a reaction tube with the length of 1200 cm and a volume of 12.2 l. The tube outside diameter was 1.315 inch (3.34 cm), with a wall thickness of 0.065 inch (0.1651 cm). In the center of the reaction tube a smaller (⅛ inch (0.3175 cm)) tube was installed, containing the thermoelements for measuring the temperature over the catalyst bed.
Feed-materials: 2.06 kg/h Propene (liquid)
3.25 kg/h 40 wt % $H_2O_2$
Solvent: 11.97 kg/h Methanol
Buffer-solution: 0.76 ml/min/h 1.0 weight % $K_2HPO_4$ (baseline)

Propene was sourced by pipeline. The precise amount was measured using a MicroMotion Coriolis mass flow sensor (model CMF010M324NQBUEZZZ). Hydrogen peroxide flow was measured by a MicroMotion Coriolis mass flow sensor (model CMF010M324NQBUEZZZ). The measurement was reported in lb/hr. The nominal concentration of the hydrogen peroxide solution was 40 weight-%. The buffer solution was fed to the reactor, using an HPLC pump. The precise amount was determined using a balance. The flow of methanol to the reactor was measured with a MicroMotion Coriolis mass flow sensor (model CMF010M324NQBUEZZZ). Nitrogen was fed as a block utility at a specification of 99.999 mol-%. The flowrate was measured using a Brooks thermal mass flow sensors (model SLAMF60S1BAA0K2A3) and reported in units of standard cubic feet per hour (scfh).

The experiments were conducted at an absolute pressure of 20 bar. The temperature in the reactor was controlled to ensure a $H_2O_2$ conversion of approximately 90%. Typical start temperature was approximately 35° C. Then the temperature was slowly ramped up to approximately 70° C. final over a run-time of 550 hours. At the beginning of the run the reactor was cooled as the exothermic heat would overheat the reactor otherwise. Towards the end of the run the reactor was heated to reach a temperature of 70° C. The buffer solution was injected into the methanol feed stream, and the resulting mixture passed over a 21-element 0.25 inch (0.635 cm) Koflo static mixer. Hydrogen peroxide and propylene were injected into the methanol stream, followed by another 21-element 0.25 inch (0.635 cm) static mixer. Feed direction was bottom to top.

The reactor effluent was fed to a first separator, where vapor and liquid were allowed to disengage. The vapor stream from the condenser was diluted with nitrogen and passed through a condenser to remove the more readily condensable species in order to prevent condensation in the lines. The liquid from the separator was fed to a distillation column consisting of a packed section (3"-schedule 40 pipe×129") and sump (6'-schedule 40 pipe by 50"). A constant level was maintained in the sump of this column by constant draw-off of liquid. The sump contained an electrical heater for heat input to the column. Vapor from the top of the column was condensed in the same cooler as the vent from the separator drum. Condensed material was collected in a drum and either returned to the column as reflux or forwarded for further processing. The pressure for the entire upstream reaction system was set by means of a pressure control valve on the overhead vapor stream from the column.

The mass flow rate of the vapor stream from the column was measured using a MicroMotion Coriolis meter (model CMF010M324NQBUEZZZ). The flow was reported in units of pounds per hour. The composition of this stream was analyzed by a gas chromatograph (GC) and reported in on a molar basis. The mass flow rate of liquid distillate from the column was measured using a MicroMotion Coriolis mass sensor (model CMF010M324NQBUEZZZ). This stream was sampled routinely. The concentration of the organic components was determined by GC analysis. The water concentration was determined by Karl Fischer titration.

The mass flow rate of the bottoms stream from the column was measured using a MicroMotion Coriolis mass sensor (model CMF010M324NQBUEZZZ). This stream was sampled routinely. The concentration of the organic components was determined by GC analysis. The water concentration was determined by Karl Fischer titration. The concentration of unreacted hydrogen peroxide was determined by a colorimetric method.

The flow rates and composition analyses of all the streams were used to determine conversions and selectivities of species of interest.

Example 2

During this experiment, dipotassium hydrogen phosphate ($K_2HPO_4$) was used as the buffer for the baseline experiments, while mixtures of $K_2HPO_4$ and 1-hydroxyethane 1,1-diphosphonic acid (HEDP) were used ($K_2HPO_4$, USP grade, from Fisher Scientific, HEDP sourced as a 60 wt % aqueous solution from Spectrum Laboratory Products) to investigate the effect of HEDP as part of the buffer system. See Table 3 below for the specific buffer combinations that were tested. All buffer solutions fed to the reactor contained 1 wt % $K_2HPO_4$.

TABLE 3

Specific buffer combinations tested

| Buffer Solution | Additive Solution flow rate [ml/min] | Time Period on Line [hrs] | $K_2HPO_4$ Flow [gmol/hr)] | $K_2HPO_4$ Ratio [μmol $K^+$/mol $H_2O_2$] | HEDP Flow [gmol/hr] | [HEDP] on a 40% $H_2O_2$ feed basis [ppmw] | HEDP Ratio [μmol HEDP/mol $H_2O_2$] |
|---|---|---|---|---|---|---|---|
| 1% $K_2HPO_4$ | 0.76 | 0 to 242, 425 to 547 | 0.00262 | 137 | 0 | 0 | 0 |
| 1% $K_2HPO_4$ + 0.25% HEDP | 0.90 | 246 to 353 | 0.00310 | 162 | 0.00066 | 42 | 17 |
| 1% $K_2HPO_4$ + 0.50% HEDP | 1.1 | 353 to 384 | 0.00379 | 198 | 0.00160 | 102 | 42 |
| 1% $K_2HPO_4$ + 0.50% HEDP | 1.25 | 384 to 425 | 0.00430 | 226 | 0.00182 | 117 | 48 |

Data was not reported for the time period from 353 to 384 hours on line because the process did not have time to achieve steady state. The following results were obtained (see Table 4 below):

TABLE 4

Results of Comparative Example 1

| Time [h] | T [° C.] | X-HP [%] | S-PO [%] | AA [%] | PM2 [%] | PM1 [%] | Ac [%] | PG [%] | O2 [%] | ROOH [%] | Buffer |
|---|---|---|---|---|---|---|---|---|---|---|---|
| 13 | 34.9 | 88.6 | 96.9 | 0.24 | 1.02 | 1.27 | 0.04 | 0.45 | 0.10 | 1.37 | 137 μmol $K^+$/mol $H_2O_2$ |

TABLE 4-continued

Results of Comparative Example 1

| Time [h] | T [° C.] | X-HP [%] | S-PO [%] | AA [%] | PM2 [%] | PM1 [%] | Ac [%] | PG [%] | O2 [%] | ROOH [%] | Buffer |
|---|---|---|---|---|---|---|---|---|---|---|---|
| 25 | 44.5 | 90.6 | 97.6 | 0.03 | 0.90 | 1.04 | 0.02 | 0.25 | 0.15 | 0.76 | 137 µmol K$^+$/mol H$_2$O$_2$ |
| 37 | 47.0 | 88.9 | 97.2 | 0.09 | 1.04 | 1.21 | 0.02 | 0.32 | 0.14 | 0.96 | 137 µmol K$^+$/mol H$_2$O$_2$ |
| 49 | 48.9 | 89.3 | 97.1 | 0.09 | 1.06 | 1.23 | 0.02 | 0.32 | 0.15 | 0.95 | 137 µmol K$^+$/mol H$_2$O$_2$ |
| 61 | 50.5 | 88.7 | 96.9 | 0.08 | 1.16 | 1.35 | 0.02 | 0.34 | 0.17 | 1.03 | 137 µmol K$^+$/mol H$_2$O$_2$ |
| 73 | 52.0 | 89.0 | 96.8 | 0.07 | 1.19 | 1.39 | 0.02 | 0.37 | 0.22 | 1.09 | 137 µmol K$^+$/mol H$_2$O$_2$ |
| 85 | 52.5 | 89.0 | 96.7 | 0.07 | 1.20 | 1.41 | 0.02 | 0.37 | 0.21 | 1.12 | 137 µmol K$^+$/mol H$_2$O$_2$ |
| 97 | 53.5 | 90.4 | 96.7 | 0.07 | 1.20 | 1.41 | 0.02 | 0.38 | 0.21 | 1.15 | 137 µmol K$^+$/mol H$_2$O$_2$ |
| 110 | 55.0 | 90.2 | 96.6 | 0.07 | 1.24 | 1.46 | 0.02 | 0.40 | 0.22 | 1.19 | 137 µmol K$^+$/mol H$_2$O$_2$ |
| 121 | 55.5 | 90.6 | 96.4 | 0.06 | 1.29 | 1.53 | 0.02 | 0.43 | 0.25 | 1.36 | 137 µmol K$^+$/mol H$_2$O$_2$ |
| 134 | 56.5 | 90.4 | 96.4 | 0.07 | 1.31 | 1.55 | 0.02 | 0.44 | 0.24 | 1.39 | 137 µmol K$^+$/mol H$_2$O$_2$ |
| 145 | 56.5 | 91.1 | 96.3 | 0.07 | 1.33 | 1.56 | 0.02 | 0.44 | 0.25 | 1.40 | 137 µmol K$^+$/mol H$_2$O$_2$ |
| 158 | 57.3 | 90.4 | 96.4 | 0.07 | 1.33 | 1.57 | 0.02 | 0.44 | 0.22 | 1.42 | 137 µmol K$^+$/mol H$_2$O$_2$ |
| 169 | 58.0 | 90.5 | 96.1 | 0.11 | 1.39 | 1.64 | 0.02 | 0.48 | 0.26 | 1.50 | 137 µmol K$^+$/mol H$_2$O$_2$ |
| 182 | 58.2 | 90.2 | 95.8 | 0.10 | 1.52 | 1.79 | 0.02 | 0.52 | 0.28 | 1.51 | 137 µmol K$^+$/mol H$_2$O$_2$ |
| 193 | 59.0 | 89.6 | 96.1 | 0.08 | 1.42 | 1.67 | 0.02 | 0.48 | 0.26 | 1.51 | 137 µmol K$^+$/mol H$_2$O$_2$ |
| 205 | 59.0 | 89.9 | 96.2 | 0.08 | 1.39 | 1.62 | 0.02 | 0.47 | 0.26 | 1.44 | 137 µmol K$^+$/mol H$_2$O$_2$ |
| 205 | 59.0 | 89.9 | 96.2 | 0.08 | 1.39 | 1.62 | 0.02 | 0.47 | 0.26 | 1.44 | 137 µmol K$^+$/mol H$_2$O$_2$ |
| 217 | 60.0 | 89.1 | 96.0 | 0.10 | 1.44 | 1.70 | 0.02 | 0.51 | 0.27 | 1.62 | 137 µmol K$^+$/mol H$_2$O$_2$ |
| 229 | 60.0 | 89.4 | 96.0 | 0.08 | 1.42 | 1.67 | 0.02 | 0.50 | 0.32 | 1.58 | 137 µmol K$^+$/mol H$_2$O$_2$ |
| 241 | 61.0 | 89.0 | 95.8 | 0.10 | 1.50 | 1.75 | 0.02 | 0.53 | 0.30 | 1.63 | 137 µmol K$^+$/mol H$_2$O$_2$ |
| 253 | 61.5 | 89.7 | 95.8 | 0.09 | 1.54 | 1.84 | 0.02 | 0.57 | 0.16 | 1.74 | (162 µmol K$^+$ + 17 µmol HEDP)/mol H$_2$O$_2$ |
| 274 | 61.5 | 91.0 | 95.9 | 0.09 | 1.48 | 1.79 | 0.02 | 0.55 | 0.18 | 1.68 | (162 µmol K$^+$ + 17 µmol HEDP)/mol H$_2$O$_2$ |
| 286 | 61.5 | 89.8 | 95.7 | 0.10 | 1.53 | 1.89 | 0.02 | 0.59 | 0.21 | 1.70 | (162 µmol K$^+$ + 17 µmol HEDP)/mol H$_2$O$_2$ |

TABLE 4-continued

Results of Comparative Example 1

| Time [h] | T [° C.] | X-HP [%] | S-PO [%] | AA [%] | PM2 [%] | PM1 [%] | Ac [%] | PG [%] | O2 [%] | ROOH [%] | Buffer |
|---|---|---|---|---|---|---|---|---|---|---|---|
| 298 | 62.6 | 89.2 | 95.4 | 0.10 | 1.61 | 1.98 | 0.02 | 0.63 | 0.22 | 1.85 | (162 µmol $K^+$ + 17 µmol HEDP)/mol $H_2O_2$ |
| 310 | 63.0 | 88.7 | 95.4 | 0.10 | 1.64 | 2.02 | 0.02 | 0.62 | 0.22 | 1.82 | (162 µmol $K^+$ + 17 µmol HEDP)/mol $H_2O_2$ |
| 322 | 64.0 | 89.7 | 95.3 | 0.10 | 1.67 | 2.03 | 0.02 | 0.63 | 0.22 | 1.81 | (162 µmol $K^+$ + 17 µmol HEDP)/mol $H_2O_2$ |
| 335 | 64.0 | 89.7 | 95.4 | 0.10 | 1.65 | 2.02 | 0.02 | 0.64 | 0.18 | 1.86 | (162 µmol $K^+$ + 17 µmol HEDP)/mol $H_2O_2$ |
| 347 | 64.5 | 89.3 | 95.4 | 0.09 | 1.65 | 2.00 | 0.02 | 0.63 | 0.18 | 1.86 | (162 µmol $K^+$ + 17 µmol HEDP)/mol $H_2O_2$ |
| 392 | 66.0 | 88.5 | 94.8 | 0.11 | 1.83 | 2.32 | 0.03 | 0.76 | 0.19 | 1.38 | (226 µmol $K^+$ + 48 µmol HEDP)/mol $H_2O_2$ |
| 404 | 67.0 | 89.7 | 94.7 | 0.10 | 1.86 | 2.32 | 0.02 | 0.76 | 0.23 | 1.39 | (226 µmol $K^+$ + 48 µmol HEDP)/mol $H_2O_2$ |
| 416 | 67.5 | 89.5 | 94.7 | 0.10 | 1.87 | 2.34 | 0.02 | 0.77 | 0.19 | 1.41 | (226 µmol $K^+$ + 48 µmol HEDP)/mol $H_2O_2$ |
| 427 | 67.9 | 89.9 | 94.4 | 0.11 | 1.98 | 2.52 | 0.02 | 0.82 | 0.18 | 1.51 | 137 µmol $K^+$/mol $H_2O_2$ |
| 439 | 68.0 | 89.0 | 94.7 | 0.13 | 1.83 | 2.20 | 0.03 | 0.76 | 0.36 | 1.38 | 137 µmol $K^+$/mol $H_2O_2$ |
| 451 | 69.0 | 90.3 | 94.9 | 0.10 | 1.79 | 2.08 | 0.02 | 0.72 | 0.36 | 1.49 | 137 µmol $K^+$/mol $H_2O_2$ |
| 463 | 69.1 | 89.5 | 94.8 | 0.15 | 1.78 | 2.09 | 0.03 | 0.74 | 0.40 | 1.54 | 137 µmol $K^+$/mol $H_2O_2$ |
| 475 | 69.5 | 89.8 | 94.9 | 0.11 | 1.77 | 2.04 | 0.03 | 0.70 | 0.40 | 1.45 | 137 µmol $K^+$/mol $H_2O_2$ |
| 487 | 70.0 | 90.2 | 94.7 | 0.14 | 1.83 | 2.11 | 0.03 | 0.74 | 0.45 | 1.53 | 137 µmol $K^+$/mol $H_2O_2$ |
| 499 | 70.0 | 89.9 | 94.8 | 0.12 | 1.79 | 2.05 | 0.03 | 0.72 | 0.47 | 1.48 | 137 µmol $K^+$/mol $H_2O_2$ |
| 511 | 70.0 | 89.3 | 94.6 | 0.13 | 1.84 | 2.11 | 0.03 | 0.75 | 0.48 | 1.57 | 137 µmol $K^+$/mol $H_2O_2$ |
| 523 | 70.5 | 90.8 | 94.8 | 0.10 | 1.79 | 2.05 | 0.02 | 0.73 | 0.45 | 1.54 | 137 µmol $K^+$/mol $H_2O_2$ |
| 535 | 70.5 | 89.2 | 94.6 | 0.15 | 1.84 | 2.12 | 0.03 | 0.76 | 0.48 | 1.60 | 137 µmol $K^+$/mol $H_2O_2$ |

TABLE 4-continued

Results of Comparative Example 1

| Time [h] | T [° C.] | X-HP [%] | S-PO [%] | AA [%] | PM2 [%] | PM1 [%] | Ac [%] | PG [%] | O2 [%] | ROOH [%] | Buffer |
|---|---|---|---|---|---|---|---|---|---|---|---|
| 547 | 71.0 | 88.9 | 94.4 | 0.13 | 1.94 | 2.22 | 0.03 | 0.79 | 0.51 | 1.65 | 137 μmol $K^+$/mol $H_2O_2$ |

Time Length of catalyst cycle/on-stream time in hours
T [° C.] Cooling water temperature in degree Celsius
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
$O_2$ [%] Selectivity to oxygen in mole-% due to hydrogen peroxide decomposition
HEDP Hydroxyethane diphosphonic acid
DKP Di-potassium-phosphate $K_2HPO_4$
$K_2$HEDP Di-potassium salt of HEDP

Results of Example 3

The graphs according to FIGS. 6 to 10 illustrate the advantage of using HEDP in comparison with the standard buffer $K_2HPO_4$ in terms of decreased by-product selectivities to oxygen. No negative effects were observed on other process measures.

Reference Example 4: Experimental Setup for Comparative Examples 2, 3 and 4 (Micro Plant)

A TS-1 catalyst as obtained according to Reference Example 1 above (140 g) was loaded into a reaction tube with the length of 180 cm and a volume of 300 ml. The tube outside diameter was ¾ inch (1.905 cm), with a wall thickness of 0.07 inch (0.19 cm). In the center of the reaction tube a smaller (⅛ inch (0.3175 cm)) tube was installed, containing the thermoelements for measuring the temperature over the catalyst bed.
Feed-materials: 54 g/h Propene (liquid)
94 g/h 40% $H_2O_2$
Solvent: 390 g/h Methanol
Buffer-solution: 0.054 g/min 1.2 weight % K-ATMP, 0.027 g/min 1.2 weight % $K_2$-ATMP (comparative example 2); 0.052 g/min 0.5 weight % $(NH_4)_4$-HEDP (comparative example 3);
0.051 g/min 0.5 weight % $(NH_4)_6$-ATMP (comparative example 4);
(flow adjusted to maintain 130-238 μmole $K^+$/mole-$H_2O_2$ or 130-238 μmole $NH_4^+$/mole-$H_2O_2$ depending on which buffer salt was used)

Propene was stored in 50 l gas-bottles, containing dip tubes, facilitating the transfer to the mini-plant by means of 25 bar nitrogen pressure. The precise amount was measured using a Brunkhorst flow meter with a 0-500 g/h range and the flow was controlled by means of a Flowserve controlvalve. Hydrogen peroxide was transferred into the reactor using a Grundfos pump $DME_2$. The amount was determined using a balance. The measurement showed liters/minute. The buffer solution was fed to the reactor using an HPLC pump. The precise amount was determined using a balance. For feeding the methanol a Lewa pump with a range of 0-1500 ml/h was used. Feed control was accomplished using a Lewa KMM. Nitrogen was fed using a Flowserve controlvalve. The amount was measured using a Brunkhorst flow meter with a range of 0-200 Nl/h.

The experiments were conducted at an absolute pressure of 20 bar. The temperature in the reactor was controlled to ensure a $H_2O_2$ conversion of approximately 90%. Typical start temperature was approximately 43° C. Then the temperature was slowly ramped up to approximately 60° C. final over a run-time of 600 hours. At the beginning of the run the reactor was cooled as the exothermic heat would overheat the reactor otherwise. Towards the end of the run the reactor was heated to reach a temperature of 60° C.

All feed-materials were introduced into the reactor tube via a ¼ inch (0.6 cm)-mixer. Feed direction was bottom to top.

The reactor effluent was passed through a 2 micrometer filter to remove fine (catalyst) particles before it was passed into the first separator. The bottom level valve controlled a level of 25% in the first separator, while the upper pressure valve set a pressure of 20 bars over the entire upstream reaction system. The second separator was also operated at a liquid level of 25%, while the upper pressure valve reduced the pressure to 2 bars.

This lower pressure served for allowing the flashing of unconverted propene, allowing a safe sample taking, and having an additional safety buffer. The two separators had a volume of 2 liters each and were kept at a temperature of 5° C., using cooling water. A nitrogen stream of 5 Nl/h was fed through the entire system (reactor→$1^{st}$ separator→$2^{nd}$ separator→vent-system) to maintain a sufficient gas flow in the direction of the vent to ascertain that traces of oxygen, formed by partial decomposition of $H_2O_2$ were flashed out and could be analyzed at the end of the vent pipe.

The samples were analyzed routinely. The concentration of the organic components was determined by GC analysis. The water concentration was determined by Karl Fischer titration. The concentration of unreacted hydrogen peroxide was determined by a colorimetric method. The flow rates and composition analyses of all the streams were used to determine conversions and selectivities of species of interest.

Reference Example 5: Synthesis of Potassium Salts of Aminotris (Methylenephosphonic Acid) (ATMP)

K-ATMP was prepared by adding 10-g of ATMP into 10-g of demineralized water, adding under continuous stirring 1.87 g of solid KOH and diluting this solution with additional demineralized water until a weight of 100-g was achieved.

$K_2$-ATMP was prepared by adding 10-g of ATMP into 10-g of demineralized water, adding under continuous stirring 3-g of solid KOH and diluting this solution with additional demineralized water until a weight of 100-g was achieved.

Reference Example 6: Synthesis of Ammonium Salts of HEDP $NH_4HEDP$ was prepared based on adding 10 g of a 60 weight-% solution of etidronic acid (HEDP) to 100 g of water, and then slowly dosing 5.1 g of a 20% NHOH solution under continuous stirring.

Reference Example 7: Synthesis of the Ammonium Salt of ATMP

A quantity of 20 g of ATMP was dissolved in 20 g of water, and a 33 weight-% solution of $NH_4OH$ was added until a pH of 6 was achieved. The resulting solution was evaporated and 24.3 g of a solid residue were obtained.

Comparative Example 2: Using K-ATMP as Buffer

During this experiment, K-ATMP was used as the buffer. A K-ATMP concentration of 130 μmole $K^+$/mole-$H_2O_2$ was adjusted until 120-hrs on-stream time, when the K-ATMP was replaced by the less acidic $K_2$-ATMP. The results are shown in Table 5 and FIGS. 11 to 13.

Results of Comparative Example 2

The graphs according to FIGS. 11 to 13 clearly illustrate the disadvantage of using the K-ATMP as well as $K_2$-ATMP in terms of increased by-product selectivities and decreased main product PO selectivity, i.e. K-ATMP as well as $K_2$-ATMP resulted in substantially lower PO-selectivities, and consequently higher PO by-product selectivities when comparing to the results of $K_2HEDP$ as of Example 1 (due to the large deviation of the results, the $K_2HEDP$ results were not graphically represented in FIGS. 11 to 13).

Comparative Example 3: Using $NH_4HEDP$ as Buffer

During this experiment, $(NH_4)_4$-HEDP was used as the buffer. An $(NH_4)_4$-HEDP concentration of 208 μmole $NH_4^+$/mole-$H_2O_2$ was adjusted and the results are summarized in the table 6 below and graphically represented in FIGS. 14 to 16.

TABLE 5

Results of Comparative Example 2-Experimental data for a potassium salt of ATMP

| Time | X-HP [%] | S-PO [%] | AA [%] | PM2 [%] | PM1 [%] | Ac [%] | PG [%] | $O_2$ [%] |
|---|---|---|---|---|---|---|---|---|
| 24 | 100 | 59.3 | 59.3 | 1.03 | 12.21 | 22.9 | 0.23 | 4.34 |
| 48 | 96 | 70.8 | 67.9 | 1.4 | 9.32 | 13.99 | 0.31 | 4.2 |
| 72 | 89.4 | 78.4 | 70.1 | 1.75 | 6.64 | 9.69 | 0.47 | 3.07 |
| 96 | 84 | 79.7 | 66.9 | 1.79 | 6.2 | 8.84 | 0.54 | 2.92 |
| 120 | 89 | 79.2 | 70.5 | 1.66 | 6.2 | 9.09 | 0.5 | 3.35 |
| 144 | 88.1 | 89.9 | 79.2 | 1.25 | 2.95 | 4.09 | 0.4 | 1.38 |
| 168 | 86.8 | 89.4 | 77.6 | 1.19 | 3.18 | 4.39 | 0.38 | 1.46 |
| 192 | 83.9 | 88.4 | 74.1 | 1.26 | 3.38 | 4.88 | 0.4 | 1.7 |
| 216 | 86.6 | 86.1 | 74.5 | 1.23 | 4.31 | 5.64 | 0.51 | 2.25 |
| 240 | 90.5 | 84.4 | 76.4 | 1.46 | 4.76 | 6.46 | 0.46 | 2.48 |
| 264 | 88.6 | 84 | 74.4 | 1.48 | 4.87 | 6.7 | 0.48 | 2.5 |
| 288 | 87.9 | 82.6 | 72.6 | 1.76 | 5.25 | 7.23 | 0.61 | 2.59 |
| 312 | 86.3 | 81.7 | 70.5 | 1.87 | 5.5 | 7.52 | 0.66 | 2.75 |
| 336 | 86.3 | 81.8 | 70.6 | 1.83 | 5.45 | 7.32 | 0.66 | 2.91 |
| 360 | 88 | 81.8 | 72 | 1.88 | 5.51 | 7.34 | 0.67 | 2.83 |
| 384 | 87.6 | 81.2 | 71.1 | 1.93 | 5.6 | 7.61 | 0.65 | 3.04 |

Time Length of catalyst cycle/on-stream time in hours
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
$O_2$ [%] Selectivity to oxygen in mole-% due to hydrogen peroxide decomposition

TABLE 6

Results of Comparative Example 3-Experimental data for NH₄HEDP

| Time | T [° C.] | X-HP [%] | S-PO [%] | AA [%] | PM2 [%] | PM1 [%] | Ac [%] | PG [%] | O₂ [%] |
|---|---|---|---|---|---|---|---|---|---|
| 23 | 43 | 99.9 | 94.6 | 0.41 | 2.12 | 2.60 | 0.07 | 0.72 | 0.10 |
| 47 | 43 | 95.9 | 96.1 | 0.55 | 1.77 | 1.91 | 0.12 | 0.59 | 0.15 |
| 71 | 43 | 90.1 | 96.0 | 0.61 | 1.51 | 1.66 | 0.15 | 0.52 | 0.15 |
| 95 | 45 | 91.5 | 95.6 | 0.62 | 1.53 | 1.67 | 0.16 | 0.51 | 0.15 |
| 119 | 46 | 91.5 | 95.6 | 0.62 | 1.54 | 1.68 | 0.16 | 0.54 | 0.15 |
| 143 | 48 | 87.2 | 95.6 | 0.74 | 1.58 | 1.82 | 0.21 | 0.57 | 0.15 |
| 167 | 51 | 90.7 | 95.6 | 0.73 | 1.76 | 1.98 | 0.22 | 0.70 | 0.15 |
| 191 | 53 | 88.5 | 96.0 | 0.81 | 1.86 | 2.14 | 0.25 | 0.77 | 0.15 |
| 215 | 57 | 87.1 | 95.7 | 0.92 | 1.94 | 2.24 | 0.28 | 0.82 | 0.15 |
| 239 | 56 | 87.1 | 96.1 | 0.94 | 2.10 | 2.33 | 0.28 | 0.84 | 0.20 |
| 263 | 58 | 92.4 | 95.8 | 1.11 | 2.20 | 2.37 | 0.30 | 0.88 | 0.20 |
| 287 | 58 | 90.5 | 95.5 | 1.14 | 2.32 | 2.66 | 0.28 | 0.96 | 0.20 |
| 311 | 59 | 86.5 | 95.3 | 1.36 | 2.24 | 2.63 | 0.36 | 0.96 | 0.20 |

Time Length of catalyst cycle/on-stream time in hours
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
O₂ [%] Selectivity to oxygen in mole-% due to hydrogen peroxide decomposition Results of Comparative Example 3

The graphs according to FIGS. 14 to 16 clearly illustrate the disadvantage of using NH₄HEDP in terms of increased by-product selectivities and decreased main product PO selectivity, i.e. NH₄HEDP resulted in substantially lower PO-selectivities, and consequently higher PO by-product selectivities when comparing to the results of K₂HEDP as of Example 1.

Comparative Example 4: Using an Ammonium Salt of ATMP as Buffer

During this experiment, [NH₄]₆ATMP was used as the buffer. An [NH₄]₆ATMP concentration of 208 μmole NH₄⁺/mole-H₂O₂ was adjusted to obtain the results shown in Table 7 and graphically represented in FIGS. 17 to 20.

TABLE 7

Results of Comparative Example 4-Experimental data for [NH₄]₆ATMP

| Time | X-HP [%] | S-PO [%] | AA [%] | PM2 [%] | PM1 [%] | Ac [%] | PG [%] | O₂ [%] |
|---|---|---|---|---|---|---|---|---|
| 24 | 100.0 | 91.2 | 0.41 | 2.65 | 4.88 | 0.08 | 0.78 | 0.1 |
| 48 | 100.0 | 94.7 | 0.58 | 1.85 | 2.22 | 0.10 | 0.54 | 0.1 |
| 72 | 92.2 | 95.5 | 0.88 | 1.47 | 1.53 | 0.16 | 0.47 | 0.1 |
| 96 | 88.5 | 95.2 | 1.07 | 1.46 | 1.55 | 0.21 | 0.47 | 0.1 |
| 120 | 89.2 | 95.1 | 1.10 | 1.51 | 1.58 | 0.22 | 0.49 | 0.1 |
| 144 | 89.2 | 95.2 | 0.97 | 1.54 | 1.56 | 0.25 | 0.51 | 0.1 |
| 168 | 89.5 | 94.5 | 1.10 | 1.70 | 1.85 | 0.26 | 0.64 | 0.1 |
| 192 | 89.4 | 94.3 | 1.09 | 1.77 | 1.92 | 0.25 | 0.67 | 0.1 |
| 216 | 91.2 | 94.0 | 1.04 | 1.88 | 2.05 | 0.25 | 0.74 | 0.1 |
| 240 | 91.2 | 93.7 | 1.13 | 1.97 | 2.21 | 0.24 | 0.79 | 0.1 |
| 264 | 91.2 | 93.6 | 1.09 | 2.02 | 2.25 | 0.24 | 0.81 | 0.1 |
| 288 | 91.2 | 93.6 | 1.09 | 2.02 | 2.25 | 0.24 | 0.81 | 0.1 |
| 312 | 91.2 | 93.5 | 1.14 | 2.03 | 2.26 | 0.26 | 0.81 | 0.1 |
| 336 | 88.5 | 93.3 | 1.17 | 2.06 | 2.29 | 0.31 | 0.85 | 0.1 |
| 360 | 89.2 | 93.2 | 1.20 | 2.09 | 2.35 | 0.29 | 0.87 | 0.1 |
| 384 | 89.2 | 92.7 | 1.25 | 2.21 | 2.56 | 0.33 | 0.93 | 0.1 |
| 408 | 88.6 | 92.1 | 1.26 | 2.40 | 2.80 | 0.33 | 1.07 | 0.1 |
| 432 | 88.0 | 92.0 | 1.24 | 2.47 | 2.91 | 0.31 | 1.10 | 0.1 |
| 456 | 88.0 | 91.8 | 1.25 | 2.51 | 2.95 | 0.32 | 1.12 | 0.15 |
| 480 | 87.6 | 92.0 | 1.25 | 2.47 | 2.91 | 0.31 | 1.10 | 0.15 |
| 504 | 88.5 | 91.8 | 1.22 | 2.50 | 2.97 | 0.33 | 1.12 | 0.15 |
| 528 | 90.5 | 91.6 | 1.25 | 2.56 | 3.09 | 0.33 | 1.12 | 0.15 |

Time Length of catalyst cycle/on-stream time in hours
X-HP [%] Conversion of hydrogen peroxide (HP) in weight percent
S-PO [%] Hydrogen peroxide based selectivity to PO in mole-%
AA [%] Hydrogen peroxide based selectivity to acetaldehyde in mole-%
PM2 [%] Hydrogen peroxide based selectivity to 1-methoxy-2-propanol in mole-%
PM1 [%] Hydrogen peroxide based selectivity to 2-methoxy-1-propanol in mole-%
Ac [%] Hydrogen peroxide based selectivity to hydroxyacetone in mole-%
PG [%] Hydrogen peroxide based selectivity to propylene glycol in mole-%
O₂ [%] Selectivity to oxygen in mole-% due to hydrogen peroxide decomposition Results of Comparative Example 4

The graphs according to FIGS. 17 to 20 clearly illustrate the disadvantage of using [NH$_4$]$_6$ATMP in terms of increased by-product selectivities and decreased main product PO selectivity, i.e. [NH$_4$]$_6$ATMP resulted in substantially lower PO-selectivities, and consequently higher PO by-product selectivities when comparing to the results of K$_2$HEDP as of Example 1.

SHORT DESCRIPTION OF THE FIGURES

CITED LITERATURE

Figure 1:
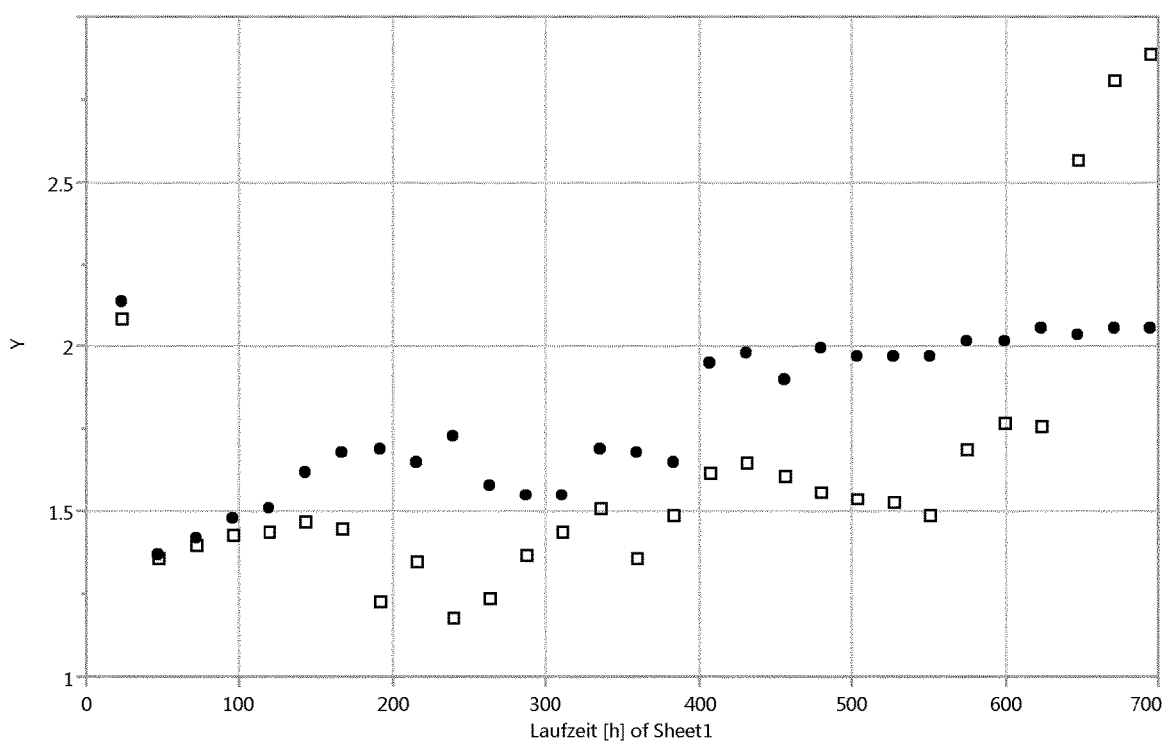
FIG. 1 shows, on the Y axis, the selectivity of 2-methoxy-1-propanol (solid circles: K$_2$HPO$_4$, rectangles: K$_2$HEDP as buffer). The x axis shows the run time in h.
Figure 2:
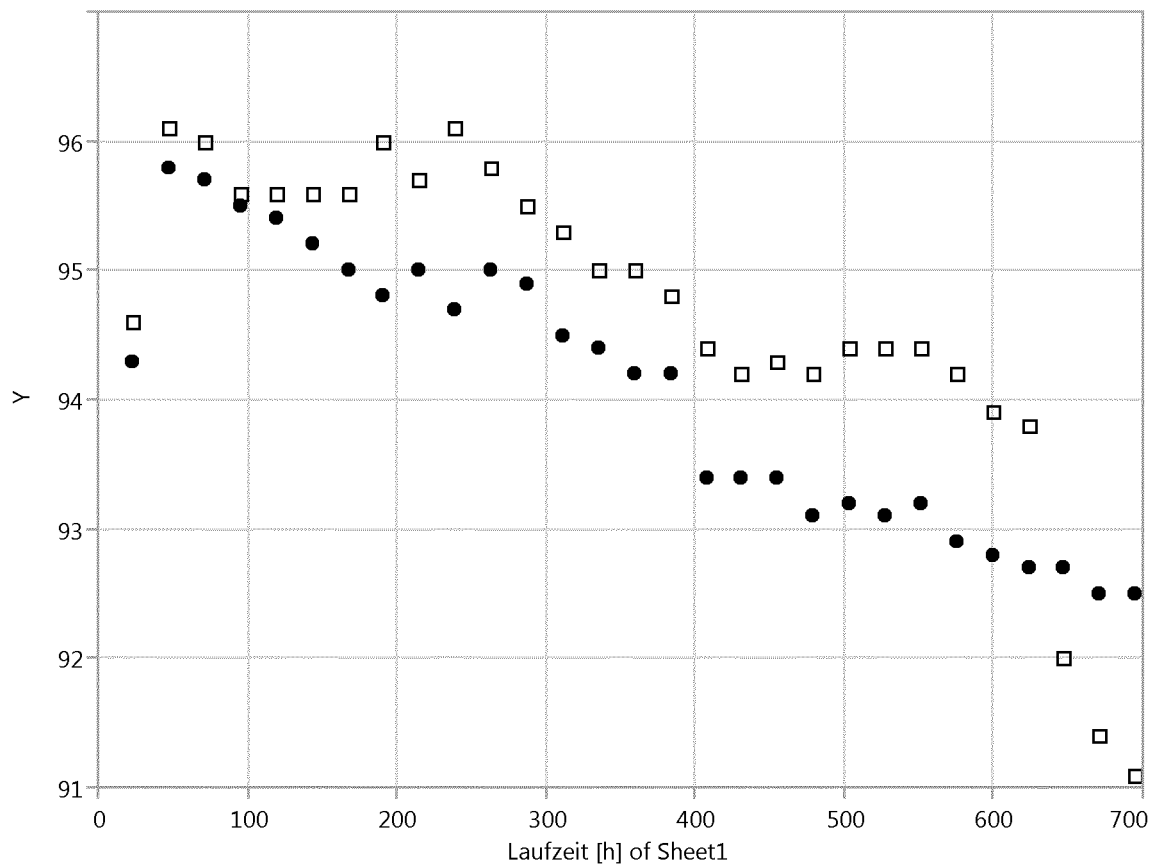
FIG. 2 shows, on the Y axis, the H$_2$O$_2$-based selectivity to PO (solid circles: K$_2$HPO$_4$, rectangles: K$_2$HEDP as buffer). The x axis shows the run time in h.
Figure 3:
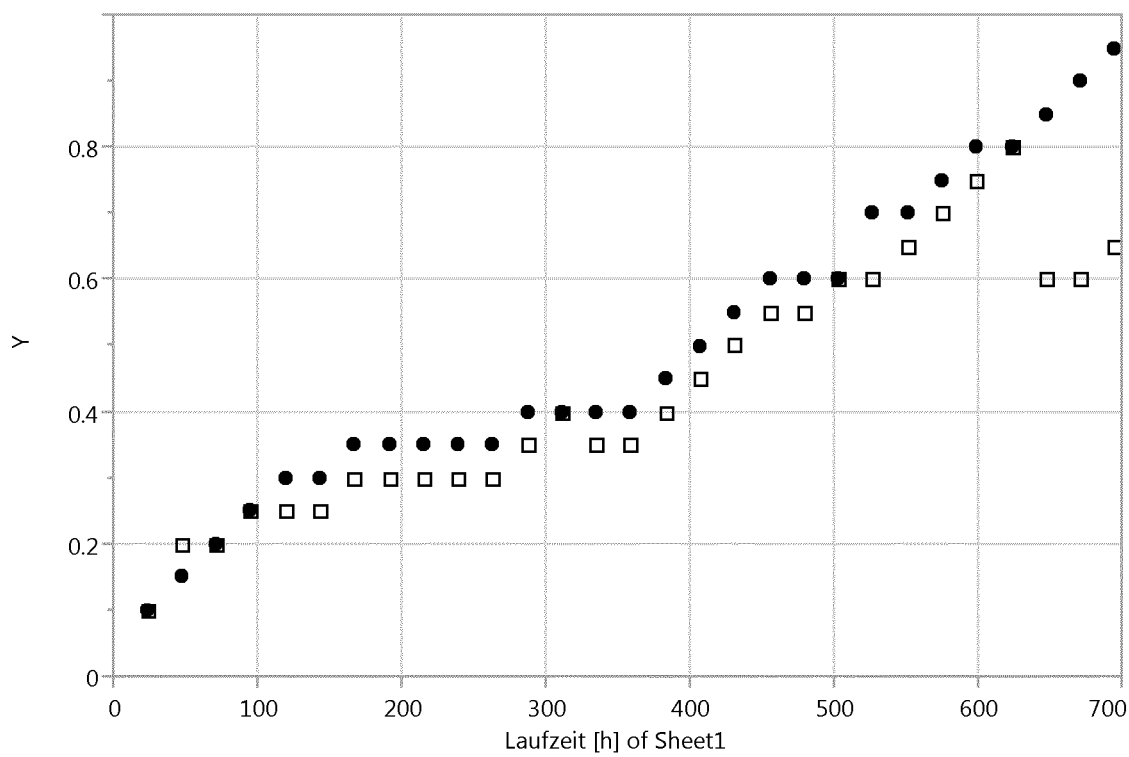
FIG. 3 shows, on the Y axis, the oxygen selectivity (solid circles: K$_2$HPO$_4$, rectangles: K$_2$HEDP as buffer). The x axis shows the run time in h.
Figure 4:
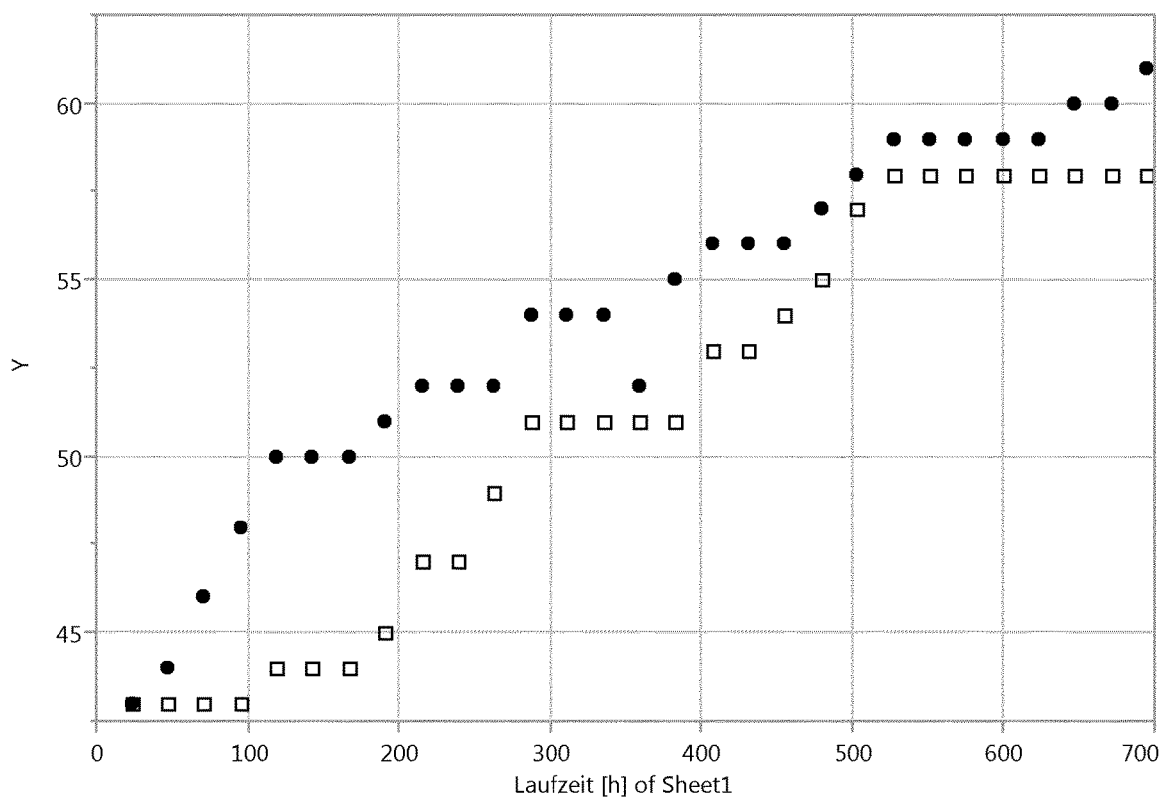
FIG. 4 shows, on the Y axis, the cooling water temperature (solid circles: K$_2$HPO$_4$, rectangles: K$_2$HEDP as buffer). The x axis shows the run time in h.
Figure 5:
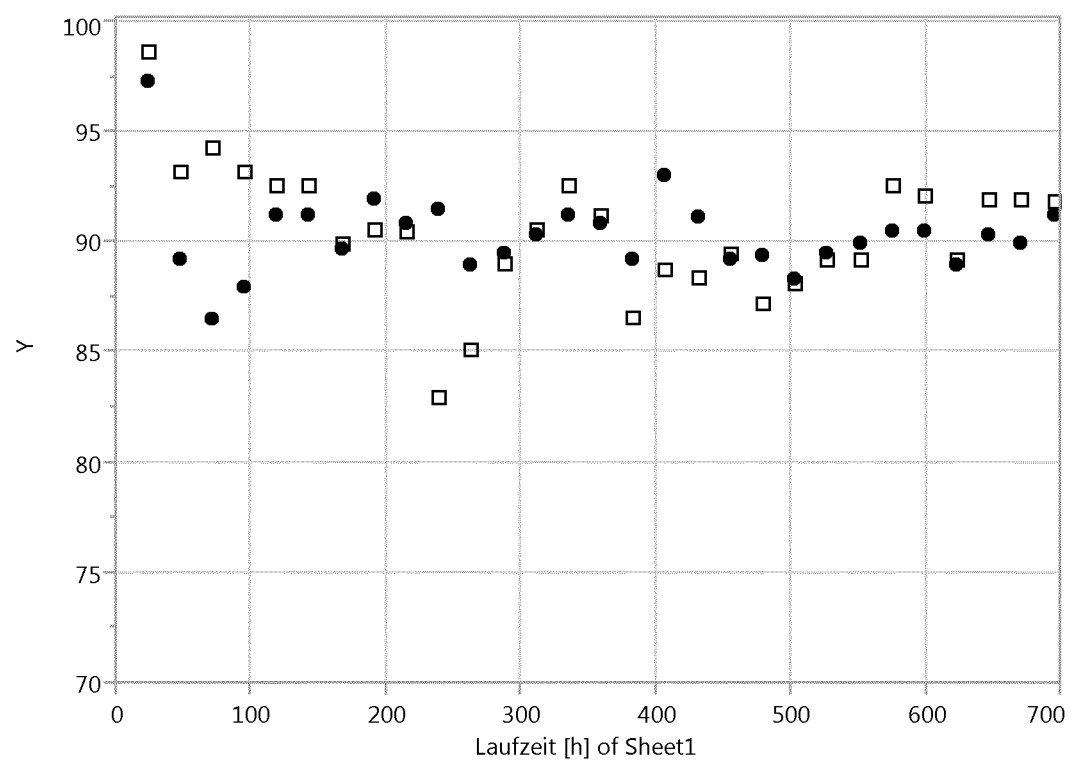
FIG. 5 shows, on the Y axis, the H$_2$O$_2$ conversion (solid circles: K$_2$HPO$_4$, rectangles: K$_2$HEDP as buffer). The x axis shows the run time in h.
Figure 6:
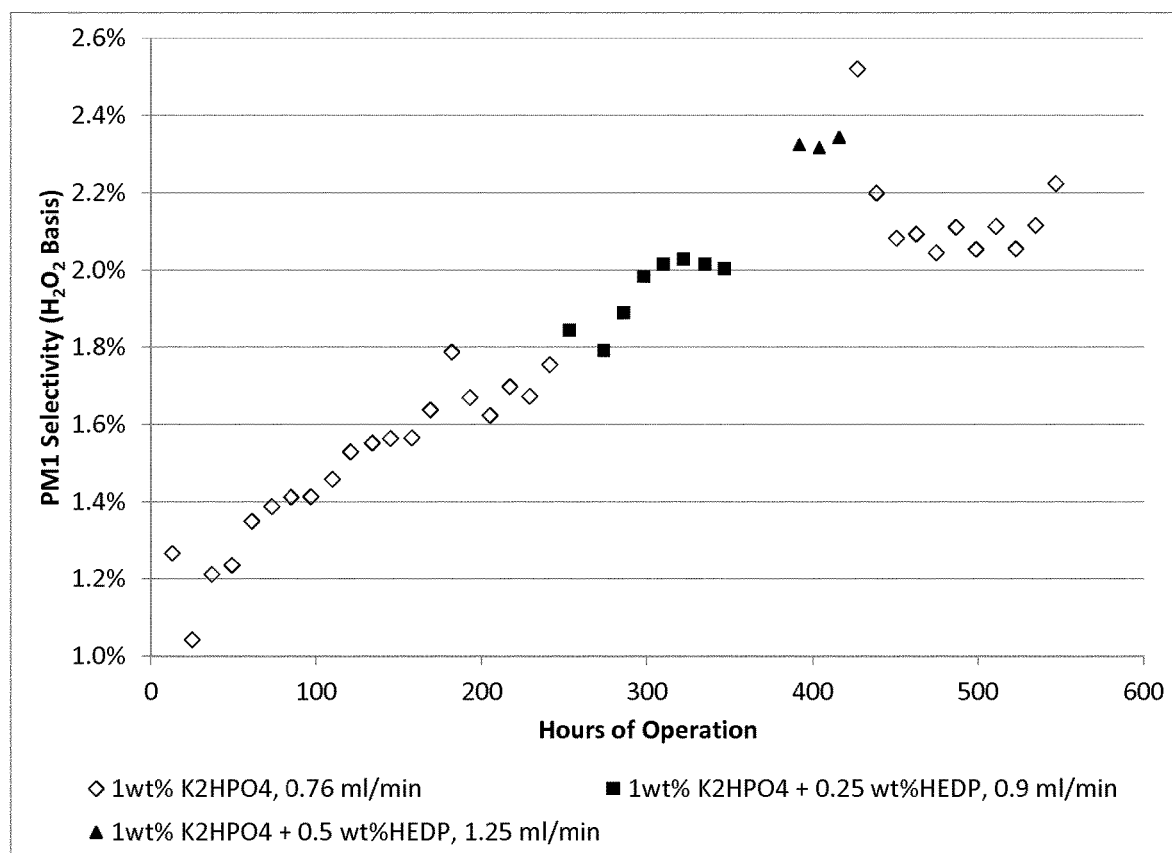
FIG. 6 shows, on the Y axis, the selectivity of 2-methoxy-1-propanol. The x axis shows the run time in h.
Figure 7:
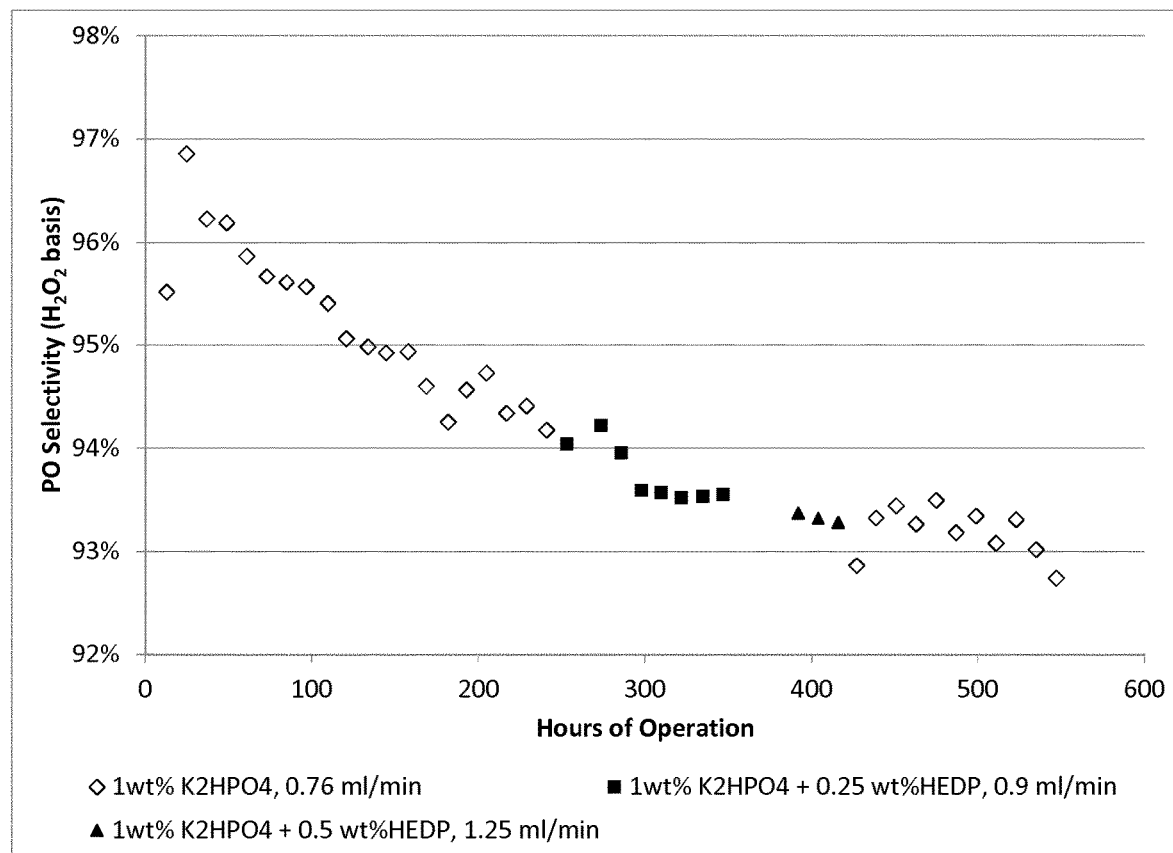
FIG. 7 shows, on the Y axis, the H$_2$O$_2$-based selectivity to PO. The x axis shows the run time in h.
Figure 8:
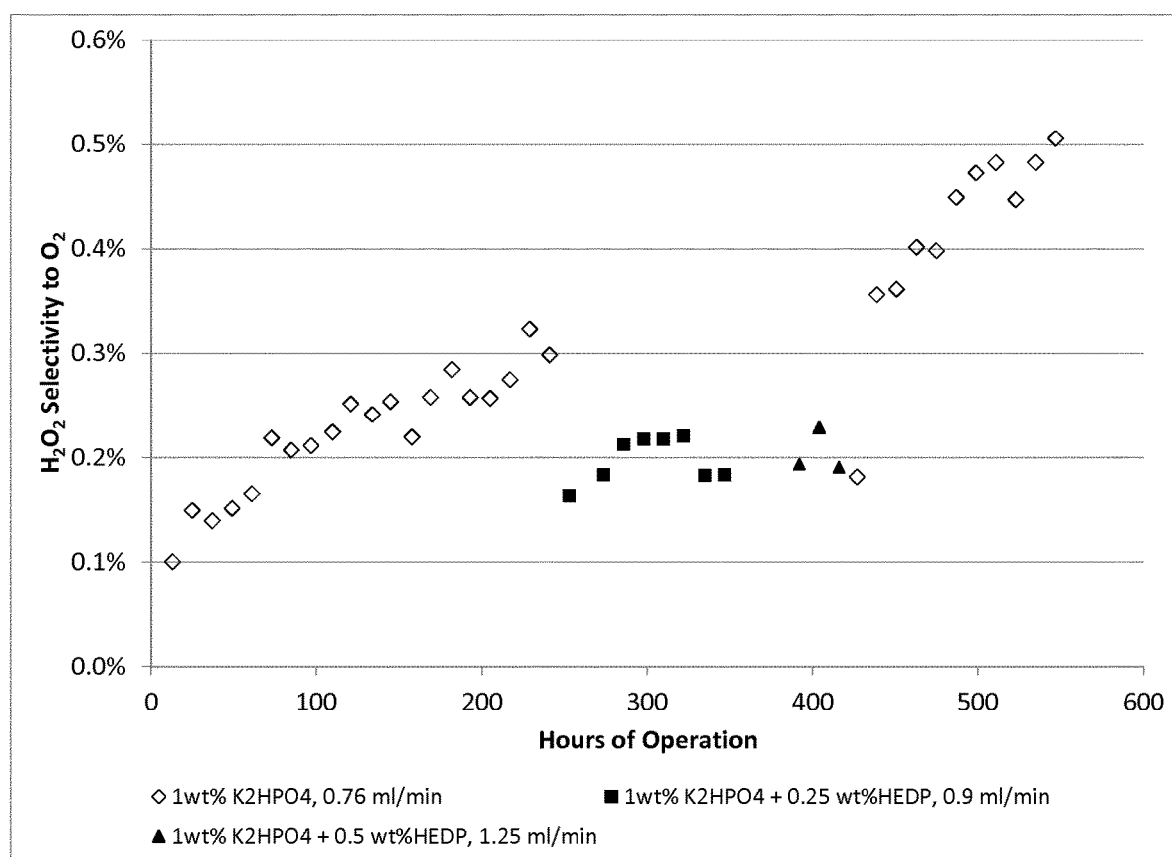
FIG. 8 shows, on the Y axis, the oxygen selectivity. The x axis shows the run time in h.
Figure 9:
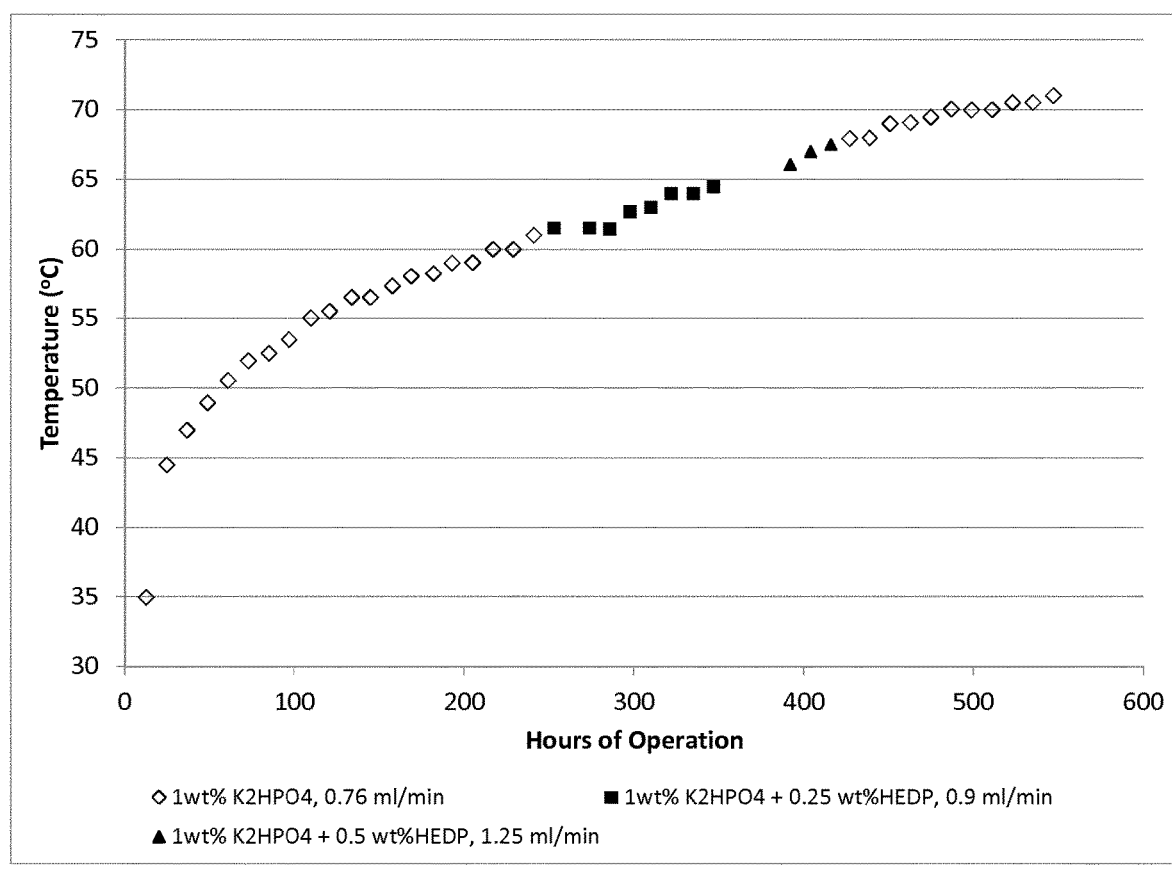
FIG. 9 shows, on the Y axis, the cooling water temperature. The x axis shows the run time in h.
Figure 10:
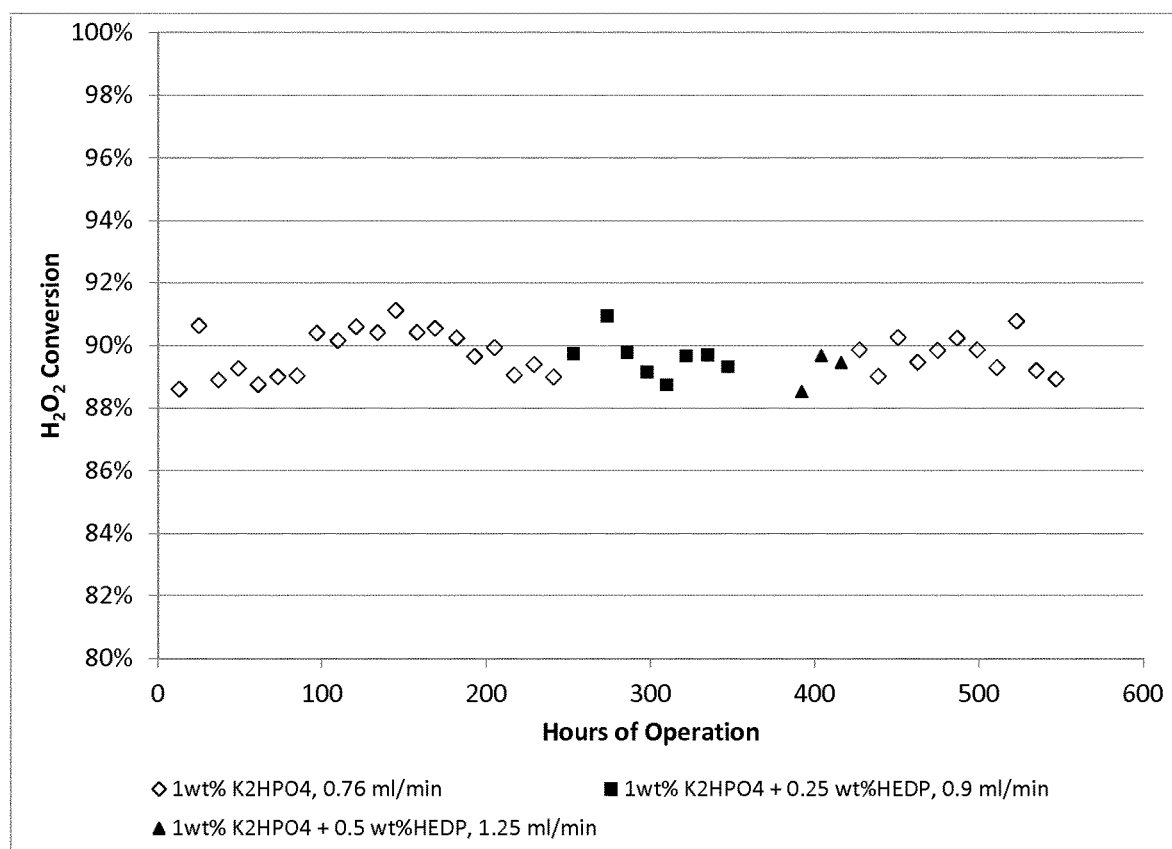
FIG. 10 shows, on the Y axis, the H$_2$O$_2$ conversion. The x axis shows the run time in h.
Figure 11:
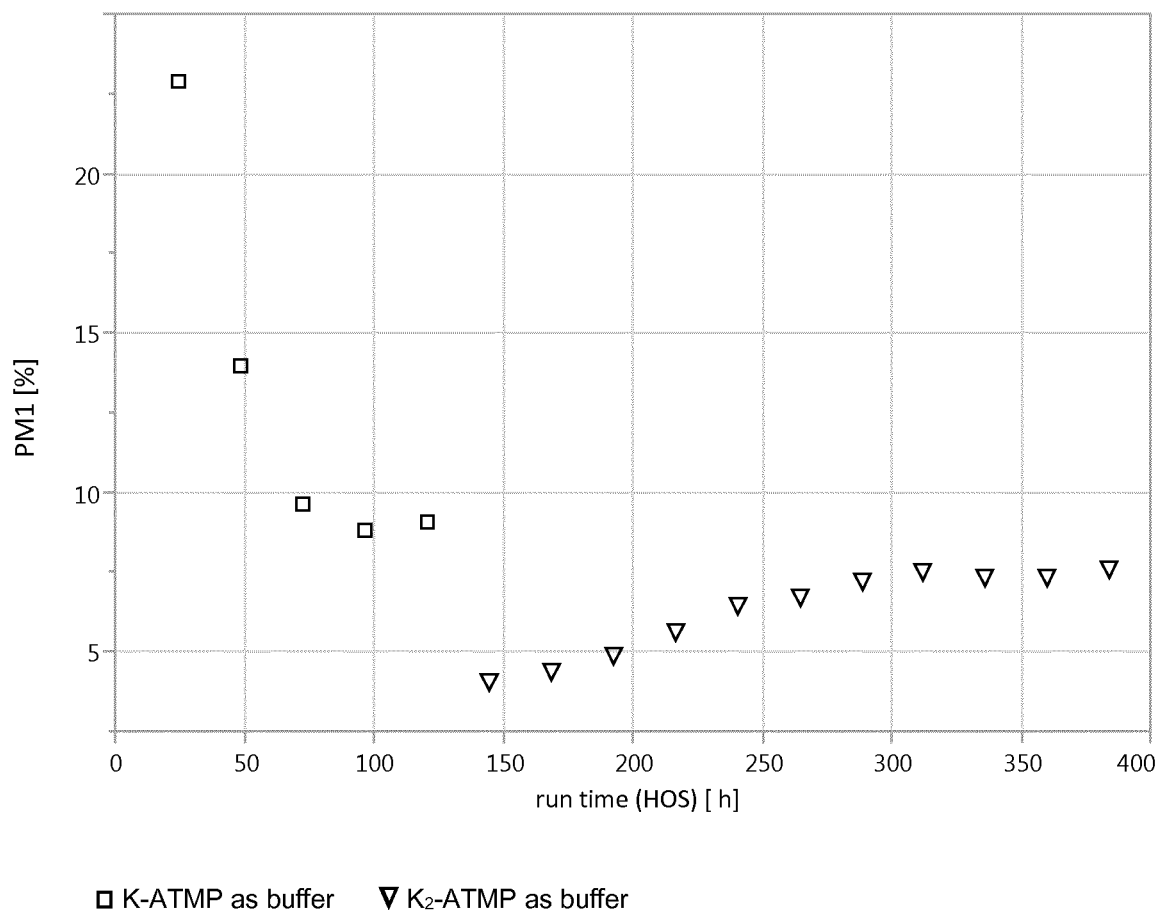
FIG. 11 shows, on the Y axis, the selectivity of 2-methoxy-1-propanol from Comparative Example 2 (rectangles: K-ATMP as buffer, triangles: K$_2$-ATMP as buffer). The x axis shows the run time in h (HOS, hours on stream).
Figure 12:
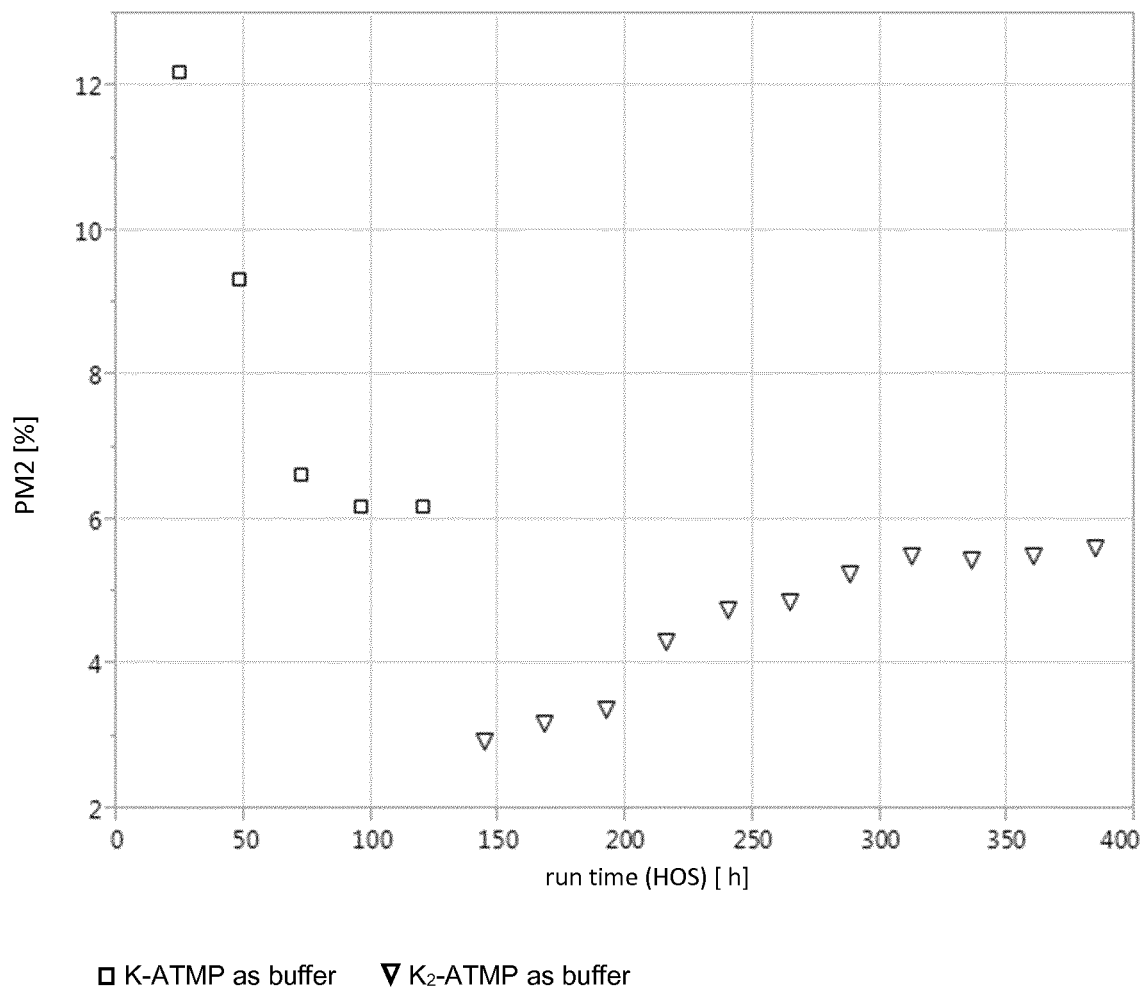
FIG. 12 shows, on the Y axis, the selectivity of 1-methoxy-2-propanol from Comparative Example 2 (rectangles: K-ATMP as buffer, triangles: K$_2$-ATMP as buffer). The x axis shows the run time in h (HOS, hours on stream).
Figure 13:
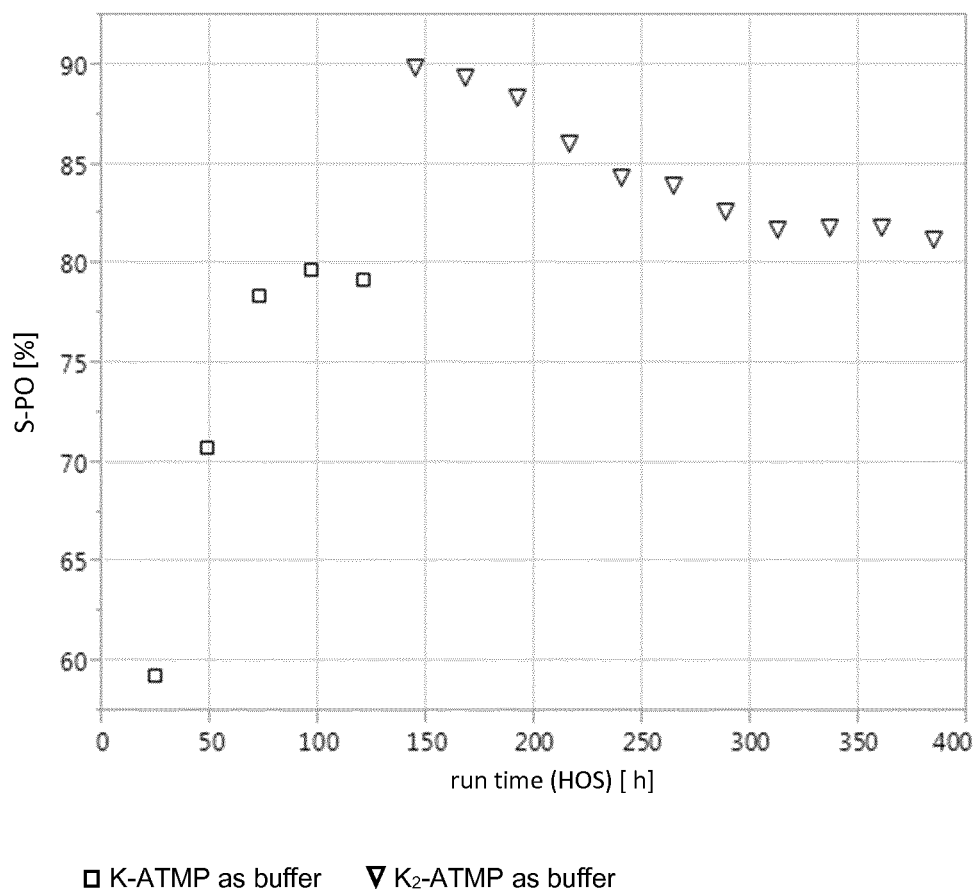
FIG. 13 shows, on the Y axis, the H$_2$O$_2$-based selectivity to PO from Comparative Example 2 (rectangles: K-ATMP as buffer, triangles: K$_2$-ATMP as buffer). The x axis shows the run time in h (HOS, hours on stream).
Figure 14:
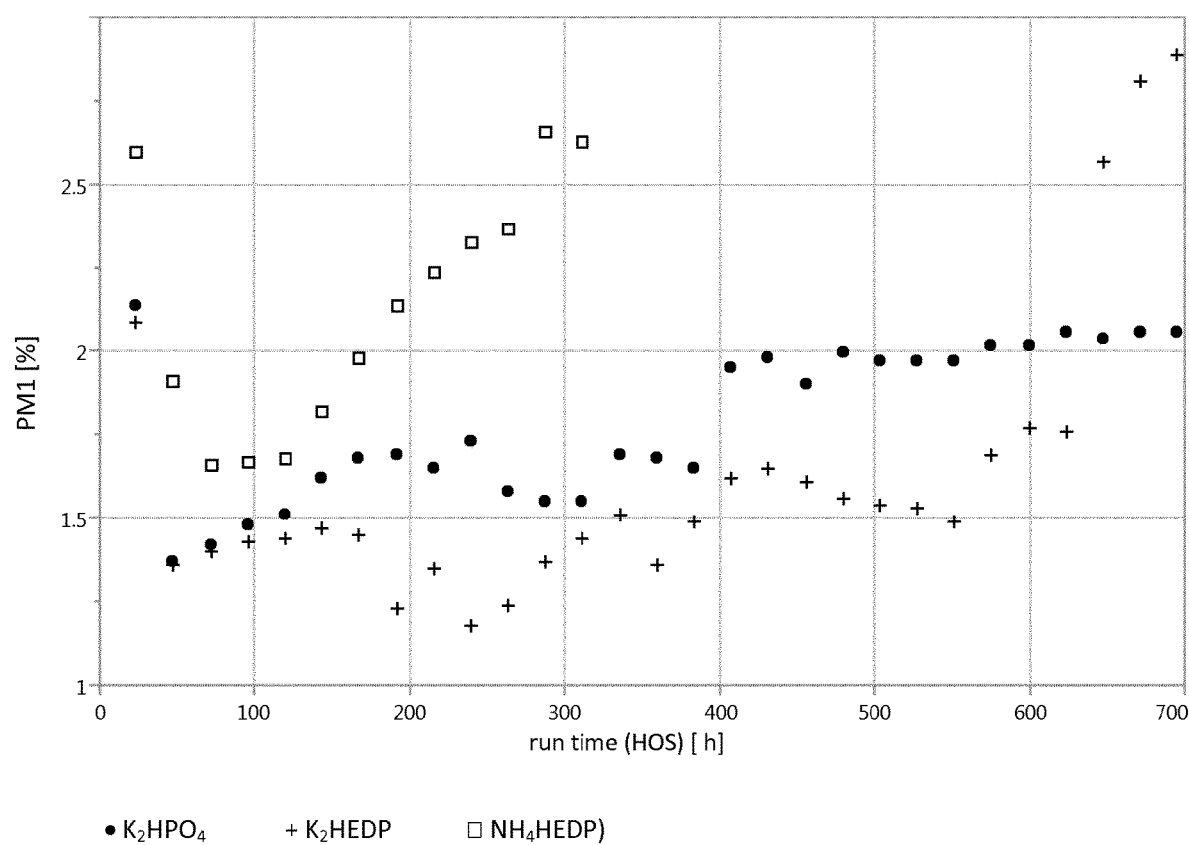
FIG. 14 shows, on the Y axis, the selectivity of 2-methoxy-1-propanol from Example 1, Comparative Example 1 and Comparative Example 3 (solid circles: K$_2$HPO$_4$, crosses: K$_2$HEDP, rectangles: NH$_4$HEDP as buffer). The x axis shows the run time in h (HOS, hours on stream).
Figure 15:
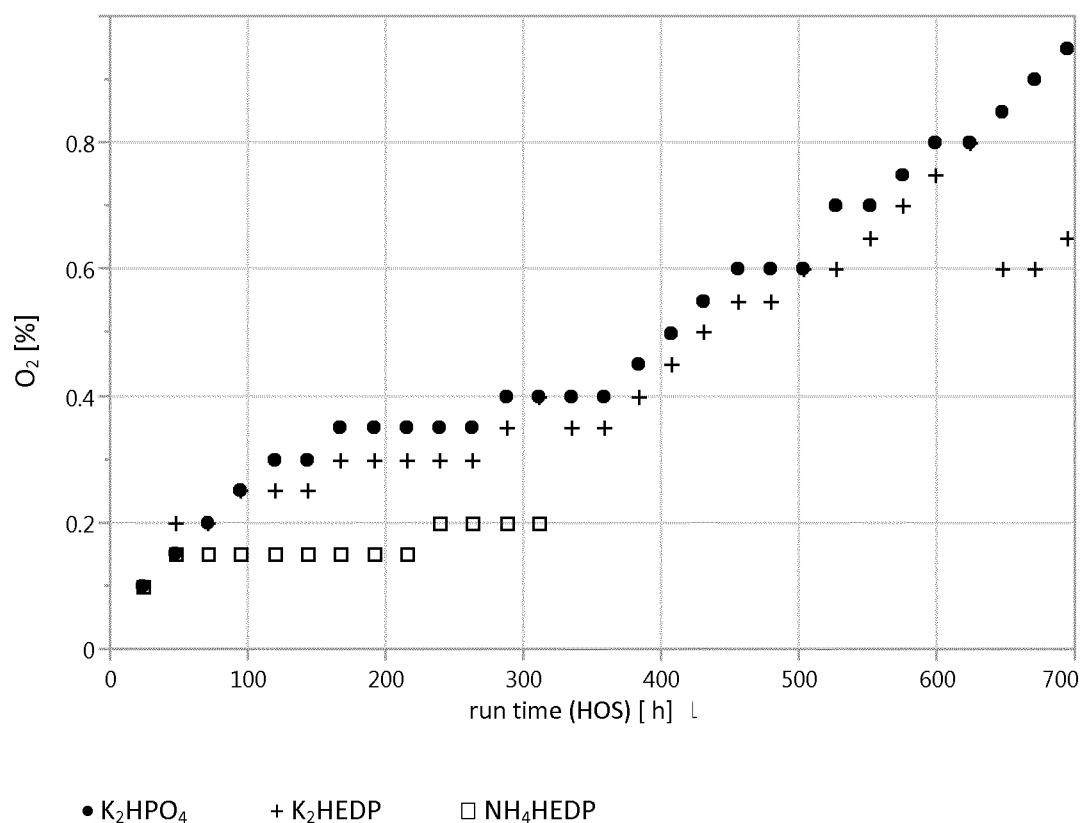
FIG. 15 shows, on the Y axis, the selectivity to oxygen from Example 1, Comparative Example 1 and Comparative Example 3 (solid circles: K$_2$HPO$_4$, crosses: K$_2$HEDP, rectangles: NH$_4$HEDP as buffer). The x axis shows the run time in h (HOS, hours on stream).
Figure 16:
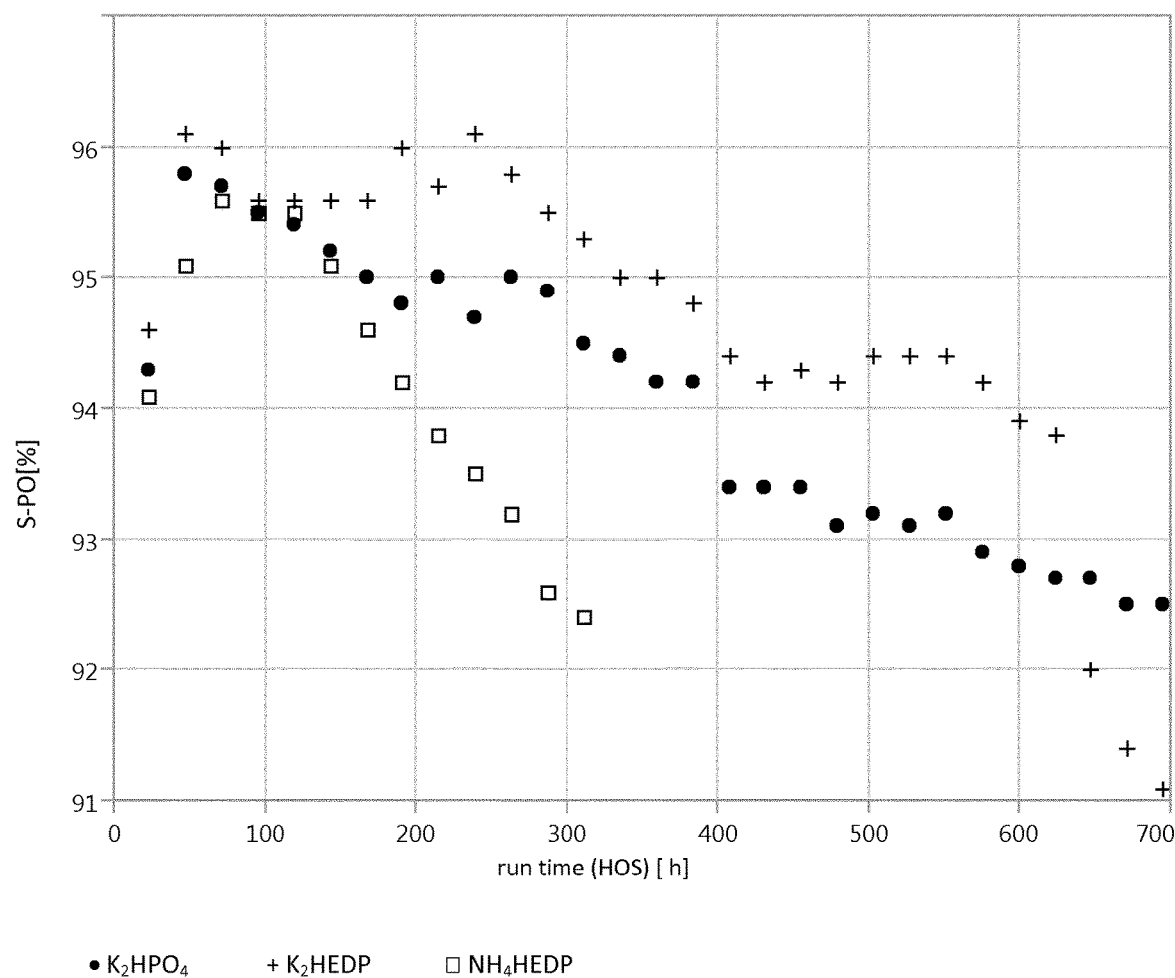
FIG. 16 shows, on the Y axis, the H$_2$O$_2$-based selectivity to PO from Example 1, Comparative Example 1 and Comparative Example 3 (solid circles: K$_2$HPO$_4$, crosses: K$_2$HEDP, rectangles: NH$_4$HEDP as buffer). The x axis shows the run time in h (HOS, hours on stream).
Figure 17:
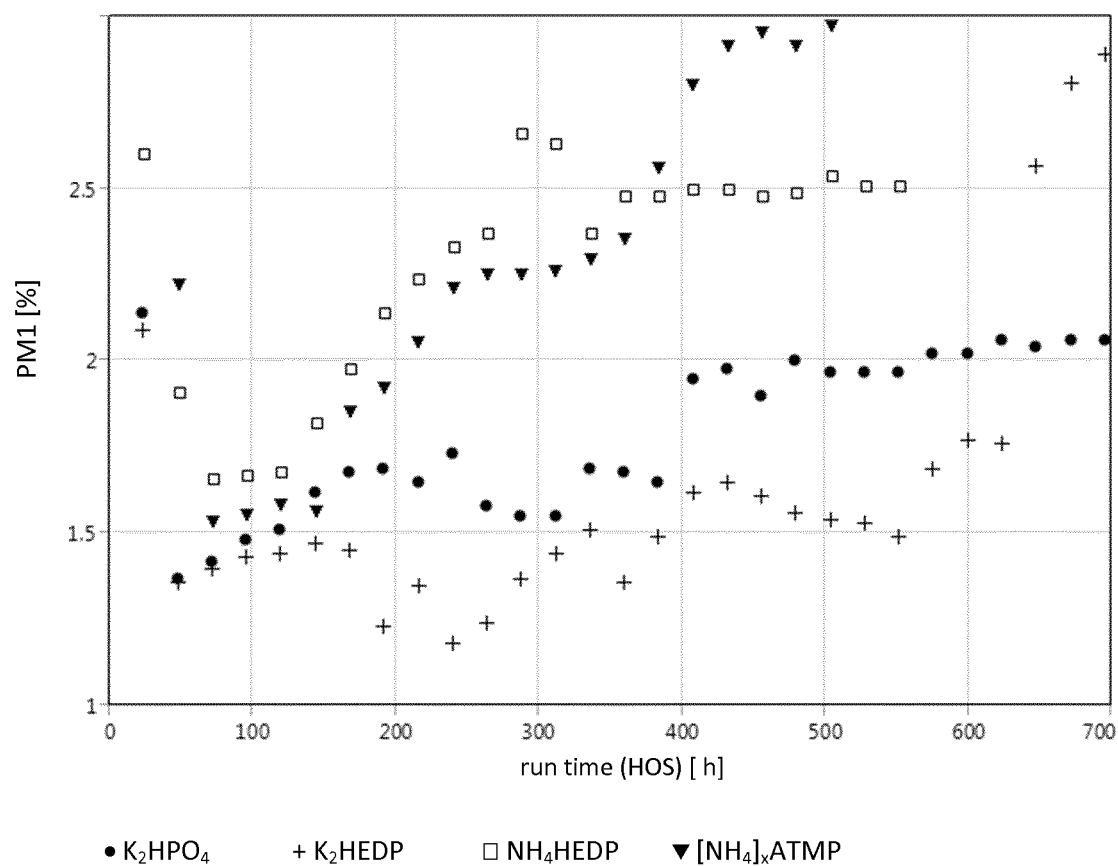
FIG. 17 shows, on the Y axis, the selectivity of 2-methoxy-1-propanol from Example 1, Comparative Example 1 and Comparative Examples 3 and 4 (solid circles: K$_2$HPO$_4$, crosses: K$_2$HEDP, rectangles: NH$_4$HEDP as buffer, triangles: [NH$_4$]$_x$ATMP as buffer). The x axis shows the run time in h (HOS, hours on stream).
Figure 18:
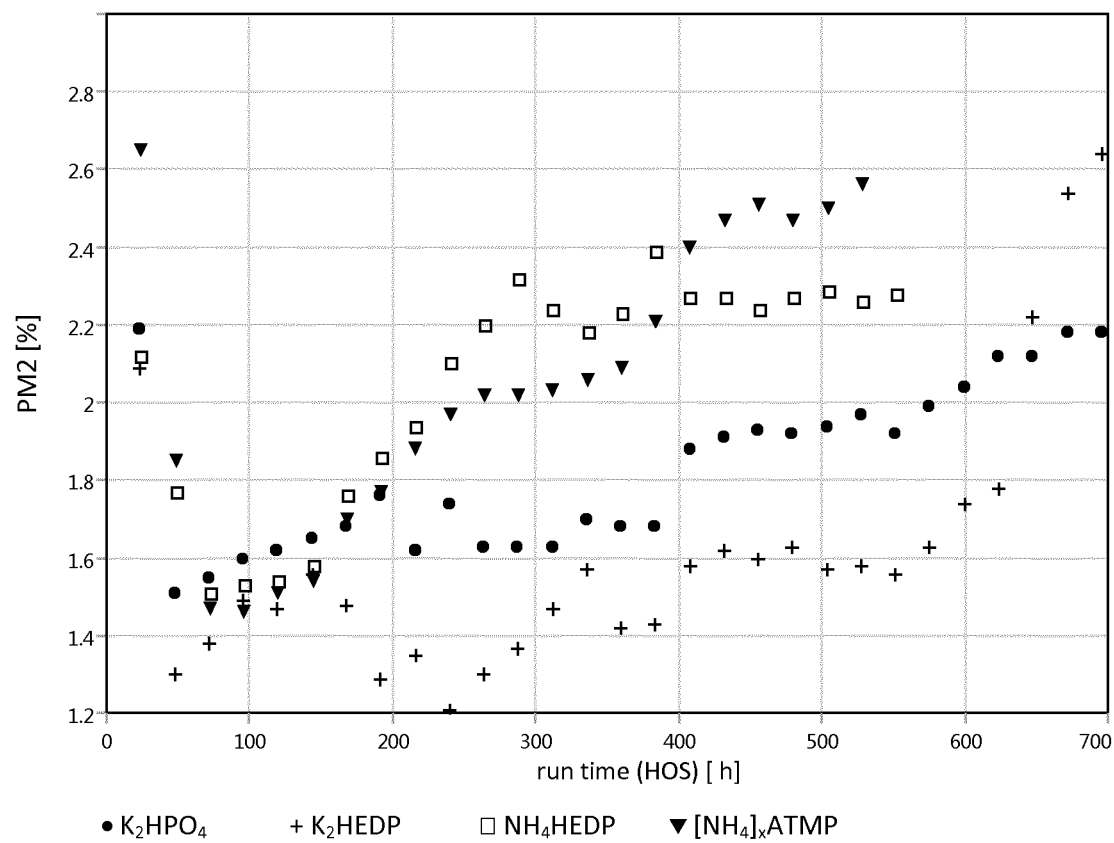
FIG. 18 shows, on the Y axis, the selectivity of 1-methoxy-2-propanol from Example 1, Comparative Example 1 and Comparative Examples 3 and 4 (solid circles: K$_2$HPO$_4$, crosses: K$_2$HEDP, rectangles: NH$_4$HEDP as buffer, triangles: [NH$_4$]$_x$ATMP as buffer). The x axis shows the run time in h (HOS, hours on stream).
Figure 19:
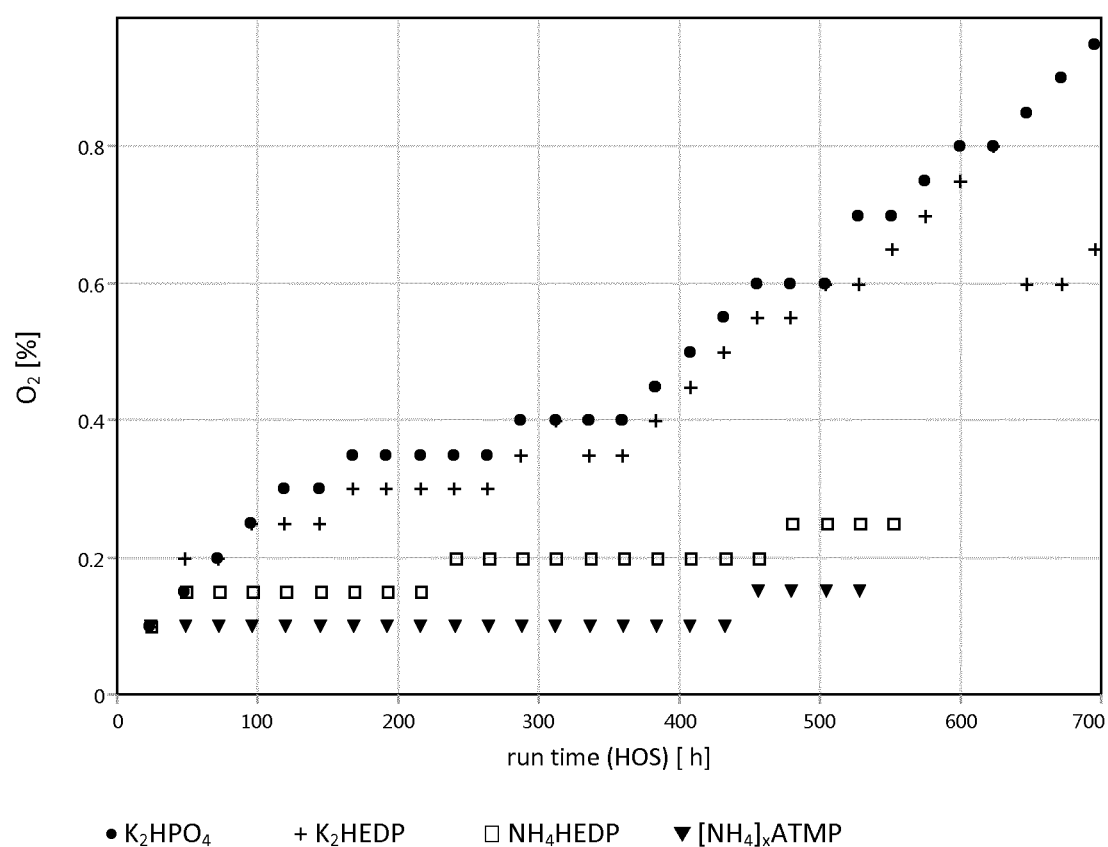
FIG. 19 shows, on the Y axis, the selectivity to oxygen from Example 1, Comparative Example 1 and Comparative Examples 3 and 4 (solid circles: K$_2$HPO$_4$, crosses: K$_2$HEDP, rectangles: NH$_4$HEDP as buffer, triangles: [NH$_4$]$_x$ATMP as buffer). The x axis shows the run time in h (HOS, hours on stream).
Figure 20:
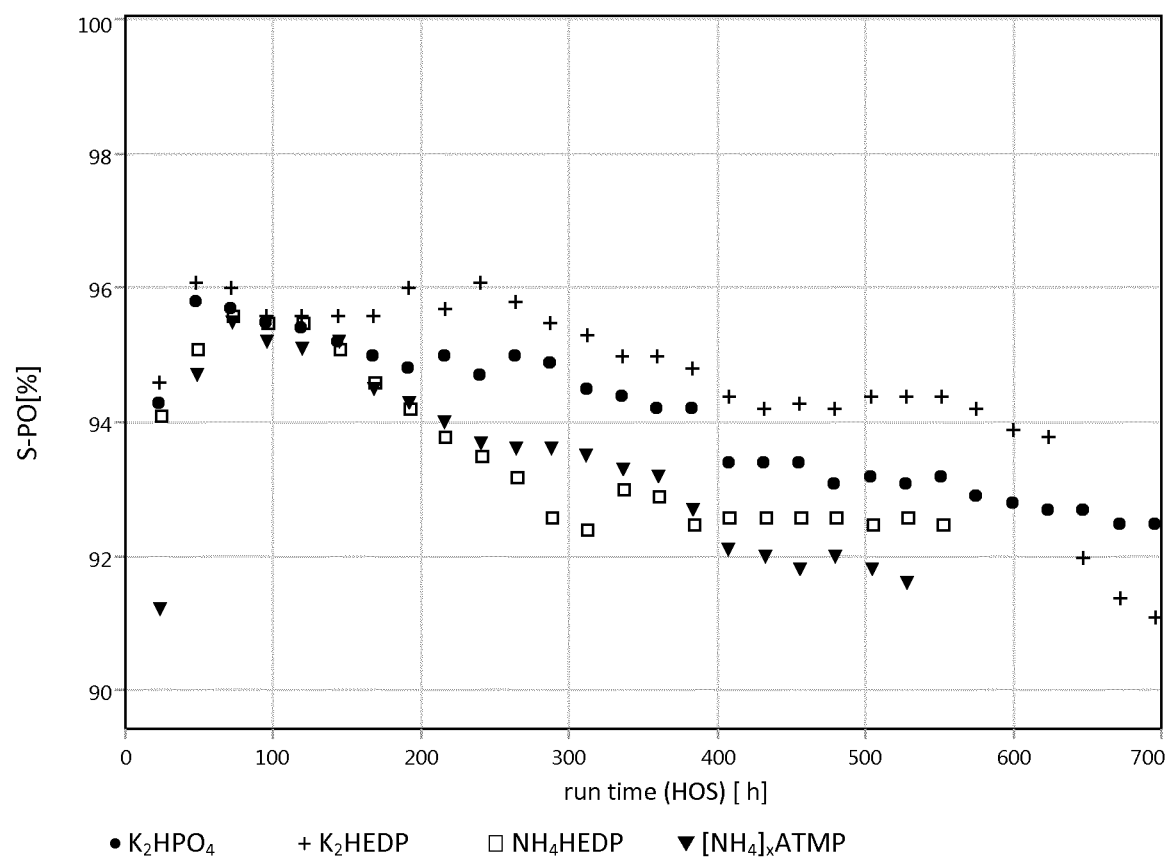
FIG. 20 shows, on the Y axis, the H$_2$O$_2$-based selectivity to PO from Example 1, Comparative Example 1 and Comparative Examples 3 and 4 (solid circles: K$_2$HPO$_4$, crosses: K$_2$HEDP, rectangles: NH$_4$HEDP as buffer, triangles: [NH$_4$]$_x$ATMP as buffer). The x axis shows the run time in h (HOS, hours on stream).

U.S. Pat. No. 4,833,260
U.S. Pat. No. 4,824,976
EP 0 757 045 A

The invention claimed is:

1. A continuous process for preparing propylene oxide, the process comprising:
   (i) passing a liquid feed stream, comprising propene, hydrogen peroxide, methanol, water, at least one dissolved potassium salt of hydroxyethylidene diphosphonic acid, and optionally propane, into an epoxidation reactor comprising a catalyst comprising a titanium zeolite of structure type MFI, and subjecting the liquid feed stream to epoxidation reaction conditions in the epoxidation reactor, to obtain a reaction mixture comprising propylene oxide, methanol, water, and the at least one dissolved potassium salt of hydroxyethylidene diphosphonic acid, and optionally propane; and removing an effluent stream from the epoxidation reactor, the effluent stream comprising propylene oxide, methanol, water, at least a portion of the at least one potassium salt of hydroxyethylidenediphosphonic acid, and optionally propane.

2. The process of claim 1, wherein the molar ratio of potassium relative to phosphorus in the at least one potassium salt of hydroxyethylidene diphosphonic acid ranges from 1:2 to 2:1.

3. The process of claim 1, wherein the at least one potassium salt of hydroxyethylidenediphosphonic acid comprises a dipotassium salt of hydroxyethylidenediphosphonic acid.

4. The process of claim 1, wherein:
   in the liquid feed stream, the molar ratio of potassium comprised in the at least one potassium salt of hydroxyethylidenediphosphonic acid relative to the hydrogen peroxide ranges from 5×10$^{-6}$:1 to 1000×10$^{-6}$:1; and
   in the liquid feed stream, the molar ratio of potassium in the liquid feed stream relative to the potassium comprised in the at least one potassium salt of hydroxyethylidenediphosphonic acid ranges from 1.2:1 to 1:1.

5. The process of claim 1, wherein, in the liquid feed stream, the molar ratio of phosphorus in the liquid feed stream relative to phosphorus comprised in the at least one potassium salt of hydroxyethylidenediphosphonic acid ranges from 1.2:1 to 1:1.

6. The process of claim 1, wherein:
the liquid feed stream passed into the epoxidation reactor has a temperature ranging from 0 to 60° C.; and
the liquid feed stream passed into the epoxidation reactor is at a pressure ranging from 14 to 100 bar.

7. The process of claim 1, wherein:
the temperature of the reaction mixture is controlled using a heat transfer medium;
the epoxidation reaction conditions comprise an epoxidation reaction temperature ranging from 10 to 100° C., wherein the epoxidation reaction temperature is defined as the temperature of the heat transfer medium prior to controlling of the temperature of the reaction mixture; and
the epoxidation reaction conditions comprise an epoxidation reaction pressure ranges from 14 to 100 bar, wherein the epoxidation reaction pressure is defined as the pressure at the exit of the epoxidation reactor.

8. The process of claim 1, wherein:
the effluent stream further comprises hydrogen peroxide and optionally propene; and
the process further comprises:
(iii) separating propylene oxide from the effluent stream, obtaining a stream being depleted in propylene oxide and comprising hydrogen peroxide, methanol, water, at least a portion of the at least one potassium salt of hydroxyethylidenediphosphonic acid, optionally propene and optionally propane;
(iv) passing the stream being depleted in propylene oxide and comprising hydrogen peroxide, methanol, water, at least a portion of the at least one potassium salt of hydroxyethylidenediphosphonic acid, optionally propene and optionally propane, obtained in
(iii) into an epoxidation reactor comprising a catalyst comprising a titanium zeolite of structure type MFI, and subjecting the stream to epoxidation reaction conditions in the epoxidation reactor, to obtain obtaining a reaction mixture comprising propylene oxide, methanol, water, the portion of the at least one dissolved potassium salt of hydroxyethylidenediphosphonic acid, and optionally propane; and
(v) removing an effluent stream from the epoxidation reactor of (iv), the effluent stream comprising propylene oxide, methanol, water, at least a portion of the portion of the at least one potassium salt of hydroxyethylidenediphosphonic acid, and optionally propane.

9. The process of claim 1 wherein the epoxidation reaction conditions comprise a hydrogen peroxide conversion ranging from 90 to 100%, wherein the hydrogen peroxide conversion is calculated based on the amount of hydrogen peroxide comprised in the effluent stream removed in (ii), relative to the amount of hydrogen peroxide comprised in the liquid feed stream in (i).

10. The process of claim 1, wherein:
the catalyst comprising a titanium zeolite of structure type MFI is present in the reactor as fixed-bed catalyst; and
the titanium zeolite of structure type MFI comprises titanium silicalite-1.

11. The process of claim 1, wherein:
the oxygen selectivity of the epoxidation reaction is at most 1.2%, wherein the oxygen selectivity is defined as the molar amount of oxygen comprised in the effluent stream removed in (ii), relative to the molar amount of hydrogen peroxide comprised in the liquid feed stream; and
the organic by-product selectivity of the epoxidation reaction is at most 9.0%,
wherein the organic by-product selectivity is defined as the molar amount of hydrogen peroxide consumed to produce the molar amount of organic by-products comprised in the effluent stream removed in (ii), relative to the total molar amount of hydrogen peroxide consumed.

12. The process of claim 1, wherein the molar ratio of potassium relative to phosphorus in the at least one potassium salt of hydroxyethylidene diphosphonic acid ranges from 1:2 to 1.5:1.

13. The process of claim 1, wherein the molar ratio of potassium relative to phosphorus in the at least one potassium salt of hydroxyethylidene diphosphonic acid ranges from 0.75:1 to 1.25:1.

14. The process of claim 1, wherein the molar ratio of potassium relative to phosphorus in the at least one potassium salt of hydroxyethylidene diphosphonic acid ranges from 0.9:1 to 1.1:1.

15. The process of claim 1, wherein, in the liquid feed stream, the molar ratio of potassium comprised in the at least one potassium salt of hydroxyethylidene-diphosphonic acid relative to the hydrogen peroxide ranges from $10 \times 10^{-6}:1$ to $700 \times 10^{-6}:1$.

16. The process of claim 1, wherein, in the liquid feed stream, the molar ratio of potassium comprised in the at least one potassium salt of hydroxyethylidene-diphosphonic acid relative to the hydrogen peroxide ranges from $10 \times 10^{-6}:1$ to $500 \times 10^{-6}:1$.

17. The process of claim 1, wherein, in the liquid feed stream, the molar ratio of phosphorus in the liquid feed stream relative to phosphorus comprised in the at least one potassium salt of hydroxyethylidenediphosphonic acid ranges from 1.1:1 to 1:1.

18. The process of claim 1, wherein, in the liquid feed stream, the molar ratio of phosphorus in the liquid feed stream relative to phosphorus comprised in the at least one potassium salt of hydroxyethylidenediphosphonic acid ranges from 1.05:1 to 1:1.

19. The process of claim 1, wherein the liquid feed stream passed into the epoxidation reactor has a temperature ranging from 25 to 50° C.

20. The process of claim 1, wherein the liquid feed stream passed into the epoxidation reactor is at a pressure ranging from 15 to 25 bar.

* * * * *